US010786680B2

(12) United States Patent
Smith

(10) Patent No.: US 10,786,680 B2
(45) Date of Patent: Sep. 29, 2020

(54) CARRYING CASE FOR AN AUTOMATED EXTERNAL DEFIBRILLATOR

(71) Applicant: Kevin Smith, West Henrietta, NY (US)

(72) Inventor: Kevin Smith, West Henrietta, NY (US)

(*) Notice: Subject to any disclaimer, the term of this patent is extended or adjusted under 35 U.S.C. 154(b) by 88 days.

(21) Appl. No.: 15/966,151

(22) Filed: Apr. 30, 2018

(65) Prior Publication Data
US 2018/0318592 A1 Nov. 8, 2018

Related U.S. Application Data

(60) Provisional application No. 62/502,198, filed on May 5, 2017.

(51) Int. Cl.
B65D 85/00 (2006.01)
A61N 1/39 (2006.01)
A45C 11/00 (2006.01)
A61F 17/00 (2006.01)
A45C 13/02 (2006.01)
A45C 11/24 (2006.01)

(52) U.S. Cl.
CPC ............ *A61N 1/3968* (2013.01); *A45C 11/00* (2013.01); *A45C 11/24* (2013.01); *A45C 13/02* (2013.01); *A61F 17/00* (2013.01); *B65D 85/70* (2013.01); *A45C 2013/026* (2013.01)

(58) Field of Classification Search
CPC ....... B65D 85/70; A61N 1/3968; A45C 11/00; A45C 13/02; A45C 2013/026; A61F 17/00
USPC ... 206/305, 320, 363, 370, 438, 37, 38, 576, 206/782; 607/5; 383/38–40, 106
See application file for complete search history.

(56) References Cited

U.S. PATENT DOCUMENTS

| | | | |
|---|---|---|---|
| 5,816,411 A * | 10/1998 | Smith | B65D 5/46096 206/782 |
| 6,390,297 B1 | 5/2002 | Hollingsworth | |
| 6,422,669 B1 | 7/2002 | Salvatori et al. | |
| 6,523,653 B2 * | 2/2003 | Roegner | A45C 3/00 190/109 |
| 6,609,026 B2 | 8/2003 | Salvatori et al. | |
| 7,600,619 B2 * | 10/2009 | Sapyta | A45C 7/0054 190/107 |
| 7,798,323 B1 | 9/2010 | McCann et al. | |
| 9,590,683 B2 | 3/2017 | Greiner | |
| 2003/0036775 A1 | 2/2003 | Salvatori et al. | |
| 2003/0038047 A1 | 2/2003 | Sleva et al. | |
| 2005/0189188 A1 * | 9/2005 | Barnes | A45C 13/02 190/110 |

(Continued)

OTHER PUBLICATIONS

Various examples of AED carrying cases found on the Web on Apr. 10, 2017. Apr. 7, 2017.

(Continued)

*Primary Examiner* — Luan K Bui
(74) *Attorney, Agent, or Firm* — Michael J. Nickerson; Basch & Nickerson LLP

(57) ABSTRACT

An automated external defibrillator soft carrying case includes a first compartment and a second compartment. The first compartment is connected to the second compartment by a hinge mechanism. The first compartment is also detachably connected to the second compartment. A first compartment ceiling is connected to the first compartment by a second hinge mechanism. The first compartment ceiling includes a transparent window.

20 Claims, 18 Drawing Sheets

(56) References Cited

U.S. PATENT DOCUMENTS

| | | | |
|---|---|---|---|
| 2005/0241972 A1 | 11/2005 | Hassett | |
| 2007/0084742 A1* | 4/2007 | Miller | A61B 17/3472 |
| | | | 206/438 |
| 2007/0241027 A1* | 10/2007 | Yang | B65D 5/4204 |
| | | | 206/580 |
| 2008/0121554 A1 | 5/2008 | Townsend | |
| 2009/0196536 A1 | 8/2009 | Young | |
| 2010/0252154 A1 | 10/2010 | Enders-Tretter | |
| 2011/0089078 A1 | 4/2011 | Ziemba | |
| 2011/0297147 A1* | 12/2011 | Lick | G09B 19/003 |
| | | | 128/202.16 |
| 2017/0203112 A1* | 7/2017 | Park | A61N 1/375 |
| 2017/0281291 A1* | 10/2017 | Garratt | A61B 50/20 |

OTHER PUBLICATIONS https://www.aeduniverse.com/Heartsine_Samaritan_Replacement_AED_Carrying_Case_p/pad-bag-01.htm Apr. 7, 2017.
http://www.aed.com/zoll-aed-plus-soft-carrying-case.html Apr. 7, 2017.
https://www.aedpeople.com/store/products/3040/Defibtech-Lifeline-View-Soft-Carrying-Case Apr. 7, 2017.
https://www.schoolhealth.com/lifepak-500-aed-carry-case Apr. 7, 2017.
http://www.aed.com/philips-fr3-soft-carrying-case.html Apr. 7, 2017.
http://www.aed.com/physio-control-lifepak-500-soft-carrying-case.html Apr. 7, 2017.
http://www.aed.com/cardiac-science-powerheart-g3-carrying-case.html Apr. 7, 2017.

\* cited by examiner

CARRYING CASE FOR AN AUTOMATED EXTERNAL DEFIBRILLATOR

PRIORITY INFORMATION

The present application claims priority, under 35 U.S.C. § 119(e), from U.S. Provisional Patent Application, Ser. No. 62/502,198, filed on May 5, 2017. The entire content of U.S. Provisional Patent Application, Ser. No. 62/502,198, filed on May 5, 2017, is hereby incorporated by reference.

BACKGROUND

An automated external defibrillator is a portable electronic device that can automatically diagnose life-threatening cardiac conditions in a patient, and is able to treat them through defibrillation.

Conventionally, automated external defibrillators have been kept with trained personnel who will attend events or are placed at public access locations, such as corporate and government offices, shopping centers, airports, stadiums, schools, community centers, or any location where people may congregate.

In addition, emergency vehicles are likely to carry automated external defibrillators. Automated external defibrillators are also increasingly common on commercial airliners, cruise ships, and other transportation facilities.

When the automated external defibrillator become mobile, it is conventionally carried in a specialized carrying case to facilitate the transport of the automated external defibrillator, as well as, provide protection thereof.

A conventional carrying case may include storage areas for related items, such as: electrode pads; gel for the electrode pads; a face shield; a pair of nitrile rubber gloves; shears; cleaning cloth; and/or a razor.

Moreover, since the automated external defibrillator is usually needed in a medical emergency, other first aid items, such as bandages, gauze, antiseptic creams, etc. may be included in the carrying case so that the responder needs only to carry a single case.

An example of a conventional automated external defibrillator carrying case, which provides a transport case for an automated external defibrillator and other conventional first aid supplies, is illustrated in FIGS. 1-6.

As illustrated in FIG. 1, a conventional automated external defibrillator soft carrying case is constructed of a first storage compartment 1 and a second storage compartment 2 with the accessibility to the first compartment 1 being enabled by using a zipper mechanism 4 and the accessibility to the second compartment 2 being enabled by using a zipper mechanism 5. The soft carrying case further includes an audio window 3 at a hinged end of the second compartment 2 to enable the transmission of the audio signals produced by an automated external defibrillator in the second compartment 2.

The first compartment 1 of the conventional automated external defibrillator soft carrying case includes a substantially flat cover 6. The exterior wall of the second compartment 2 of the conventional automated external defibrillator soft carrying case includes a handle 24 and an attachment ring 23. It is further noted that the height 21 of the first compartment 1 is equal in height to the height 22 of the second compartment 2.

As illustrated in FIG. 2, the first compartment 1 can be accessed by opening the zipper mechanism 4, which allows the cover 6 to be moved away from the internal volume of the first compartment 1. The cover 6 is connected to a side wall of the first compartment 1 by a hinge mechanism 25, wherein the hinge mechanism 25 may be the outer casing of the conventional automated external defibrillator soft carrying case. Within the first compartment 1, a securable storage area 8 is constructed on the cover 6. Moreover, a floor of the first compartment 1 includes securable storage areas 7. A securable storage area is an area that allows the items to be secured in place or contained to a certain area or volume.

As illustrated in FIG. 3, the second compartment 2 can be accessed by opening the zipper mechanism 5, which allows the first compartment 1 to be moved away from the internal volume of the second compartment 2, via a hinge mechanism 25, wherein the hinge mechanism 25 may be the outer casing of the conventional automated external defibrillator soft carrying case. The hinge mechanism 25 is connected to floor/sidewall of the first compartment 1 and a sidewall of the second compartment 2. Within the second compartment 2, a securable storage area 9 is constructed on the opposite side of the floor (19) of the first compartment 1. Moreover, the second compartment 2 includes a hinge 12 for a false floor or divider 10 having storage areas 11 thereon.

FIG. 4 illustrates the area of the second compartment 2 of the conventional automated external defibrillator soft carrying case below the false floor or divider 10. This area of the second compartment 2 of the conventional automated external defibrillator soft carrying case can stored an automated external defibrillator. The area includes a strap 13 or other mechanism for securing the automated external defibrillator when enclosed in the second compartment 2.

The second compartment 2 includes an audio window 3 to allow the sounds (alarms or audio instruction) of the automated external defibrillator to properly propagate to the environment so that the user can perceive the sounds of the automated external defibrillator. The opposite side of the false floor or divider 10 includes a secured storage area 14.

The positioning of the first compartment 1 with respect to the second compartment 2 to allow access to the second compartment 2, by rotating the first compartment 1 away from the second compartment 2, via hinge mechanism 19, causes a torque or force 15, which may cause the conventional automated external defibrillator soft carrying case to tip over or the floor of the second compartment 2 to lift up, as illustrated in FIG. 5.

In other words, the center of gravity of the conventional automated external defibrillator soft carrying case shifts towards the position of the first compartment 1 to make the conventional automated external defibrillator soft carrying case unstable or the floor of the second compartment 2 to lift up, which may be problematic when using or operating an automated external defibrillator while the automated external defibrillator is secured in the carrying case.

Moreover, even if weight is added to the second compartment to prevent the shifting of the center of gravity, the first compartment 1 will be biased (16) to close upon the second compartment 2, as illustrated in FIG. 6.

Therefore, it is desirable to provide an automated external defibrillator soft carrying case which is stable when using or operating the automated external defibrillator while the automated external defibrillator is secured in the carrying case.

BRIEF DESCRIPTION OF THE DRAWINGS

The drawings are only for purposes of illustrating various embodiments and are not to be construed as limiting, wherein.

DETAILED DESCRIPTION

Figure 1:
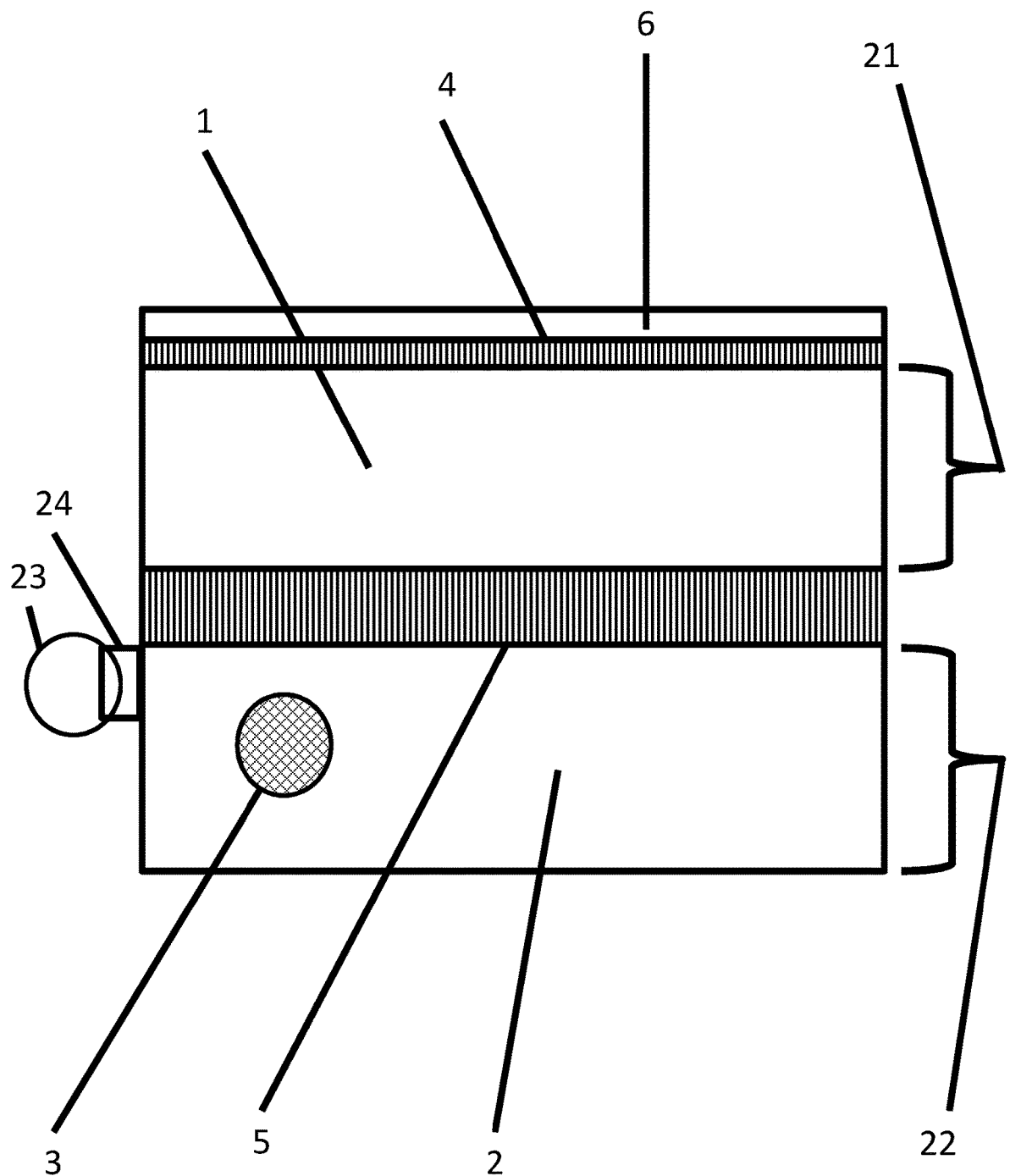
FIG. 1 shows a side perspective view of a conventional automated external defibrillator soft carrying case.
Figure 2:
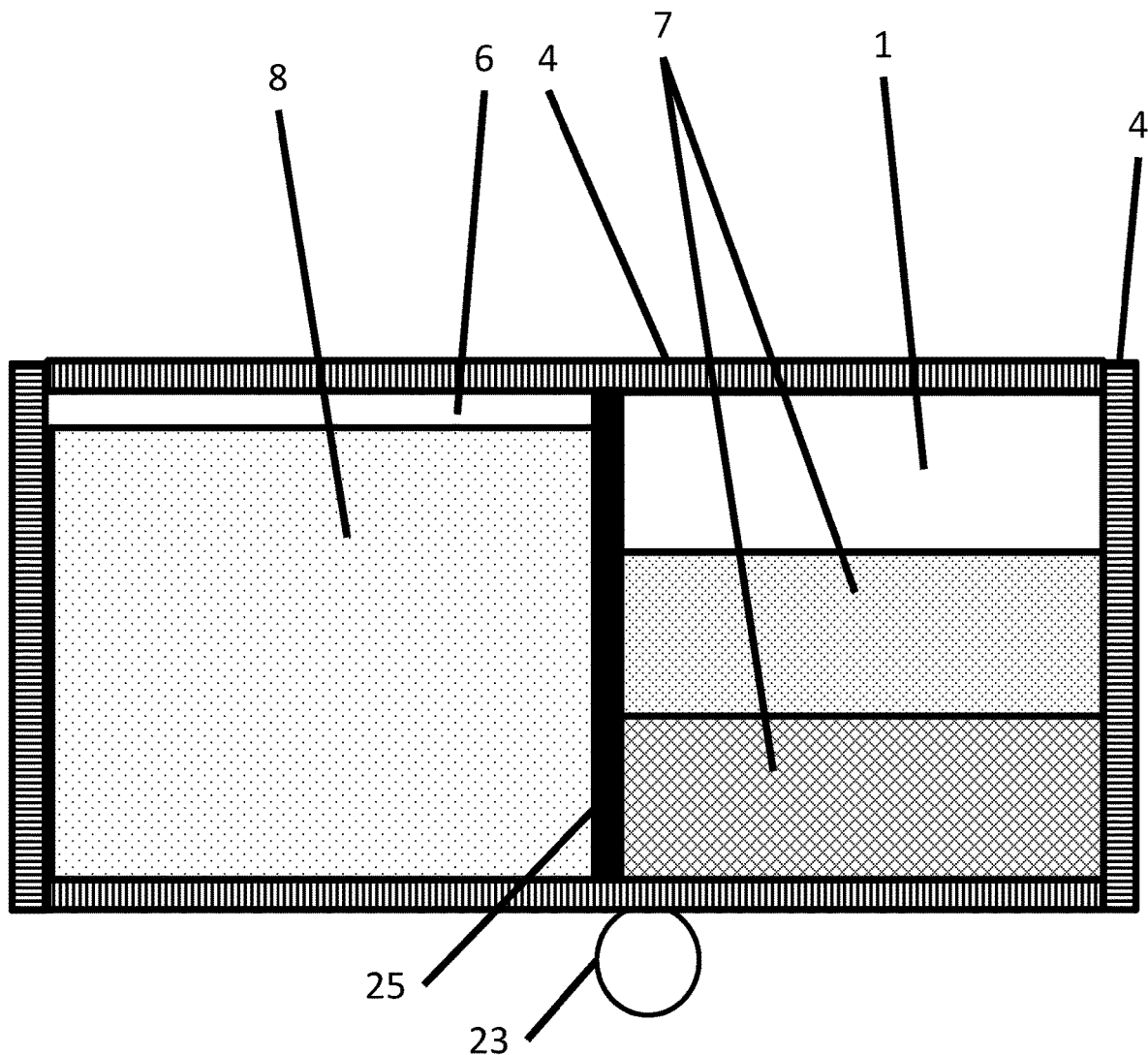
FIG. 2 shows a first compartment of the conventional automated external defibrillator soft carrying case of FIG. 1.
Figure 3:
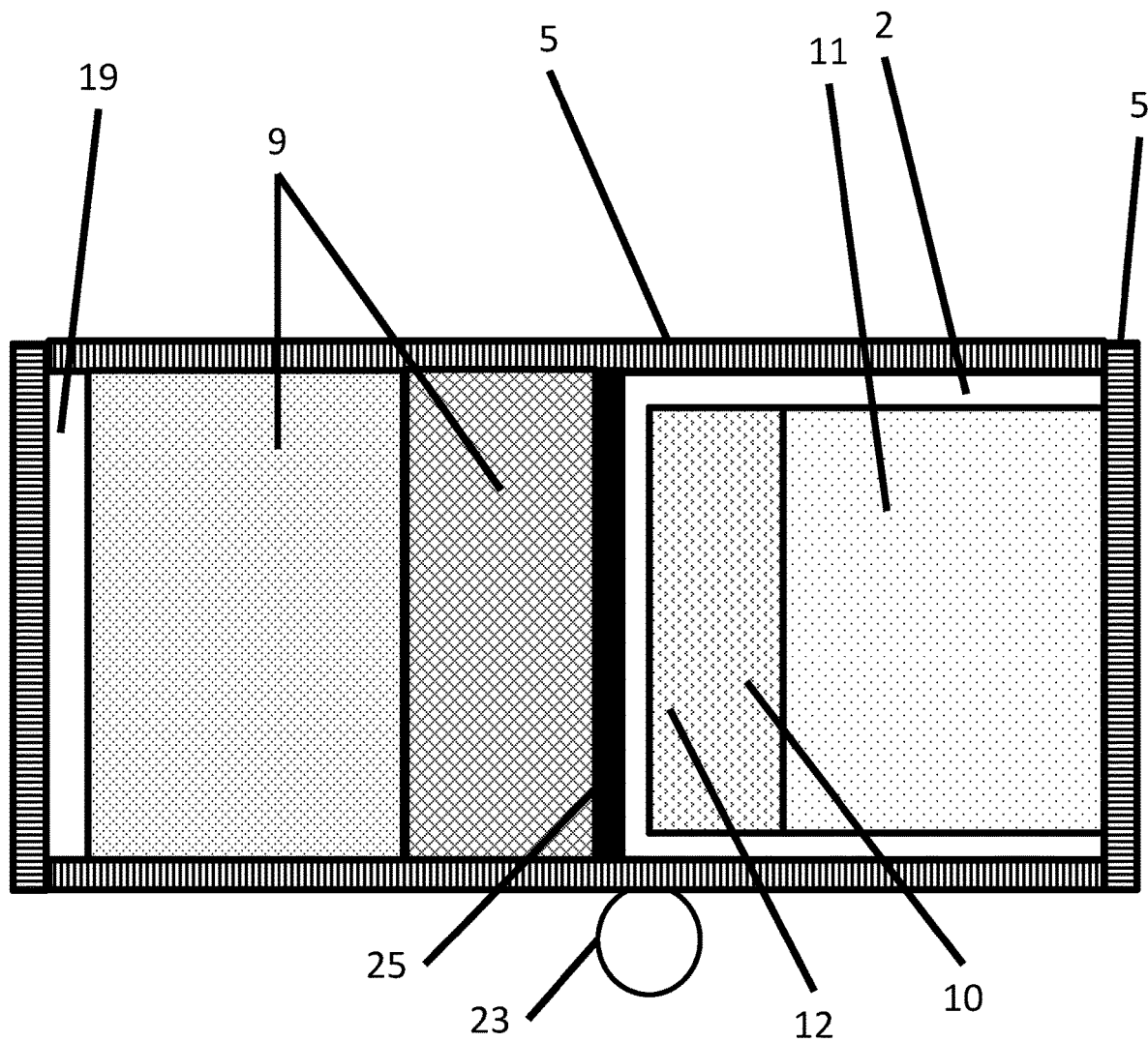
FIG. 3 shows a second compartment of the conventional automated external defibrillator soft carrying case of FIG. 1.
Figure 4:
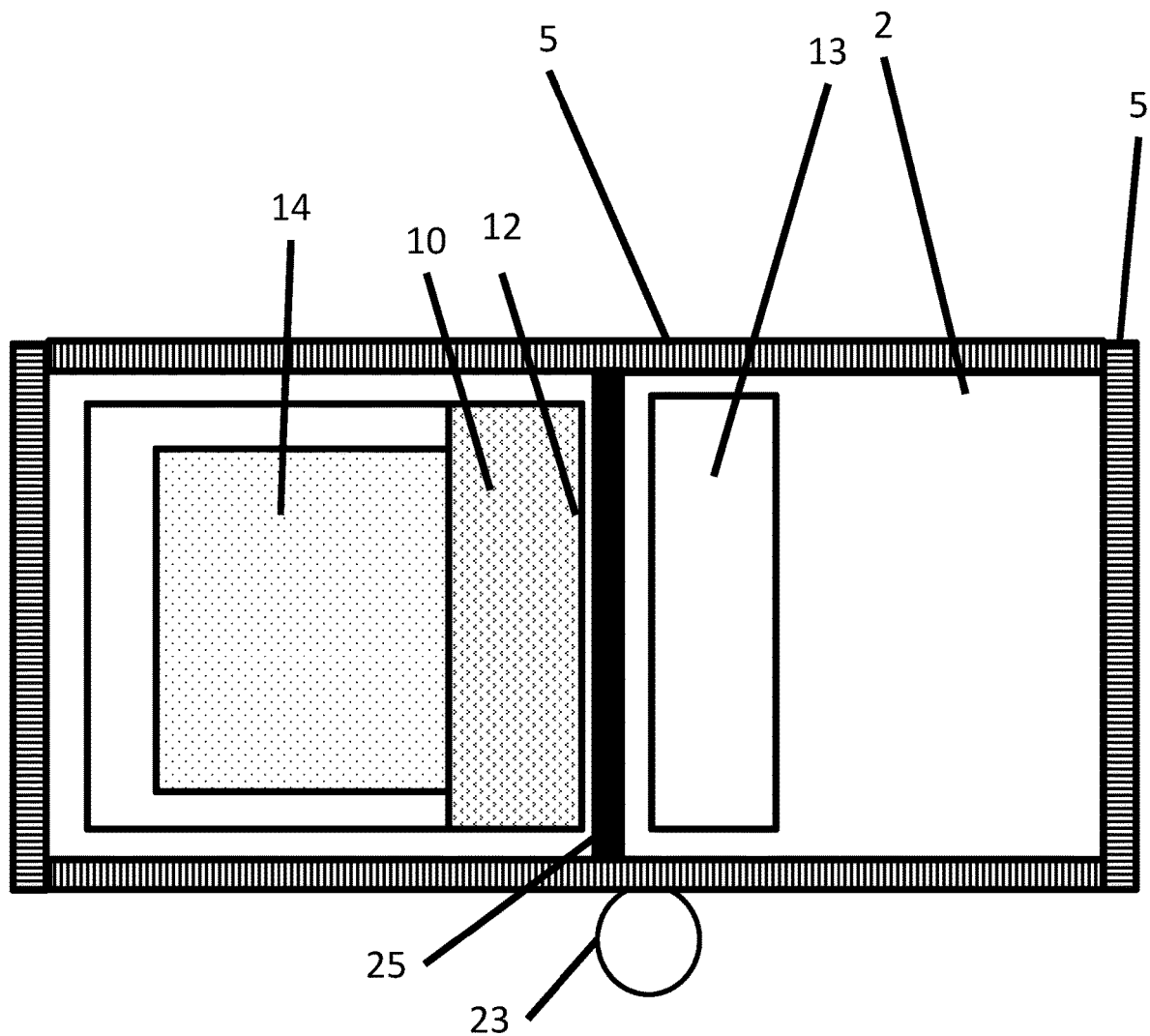
FIG. 4 shows another perspective of the second compartment of the conventional automated external defibrillator soft carrying case of FIG. 1.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts may be properly illustrated.

Figure 7:
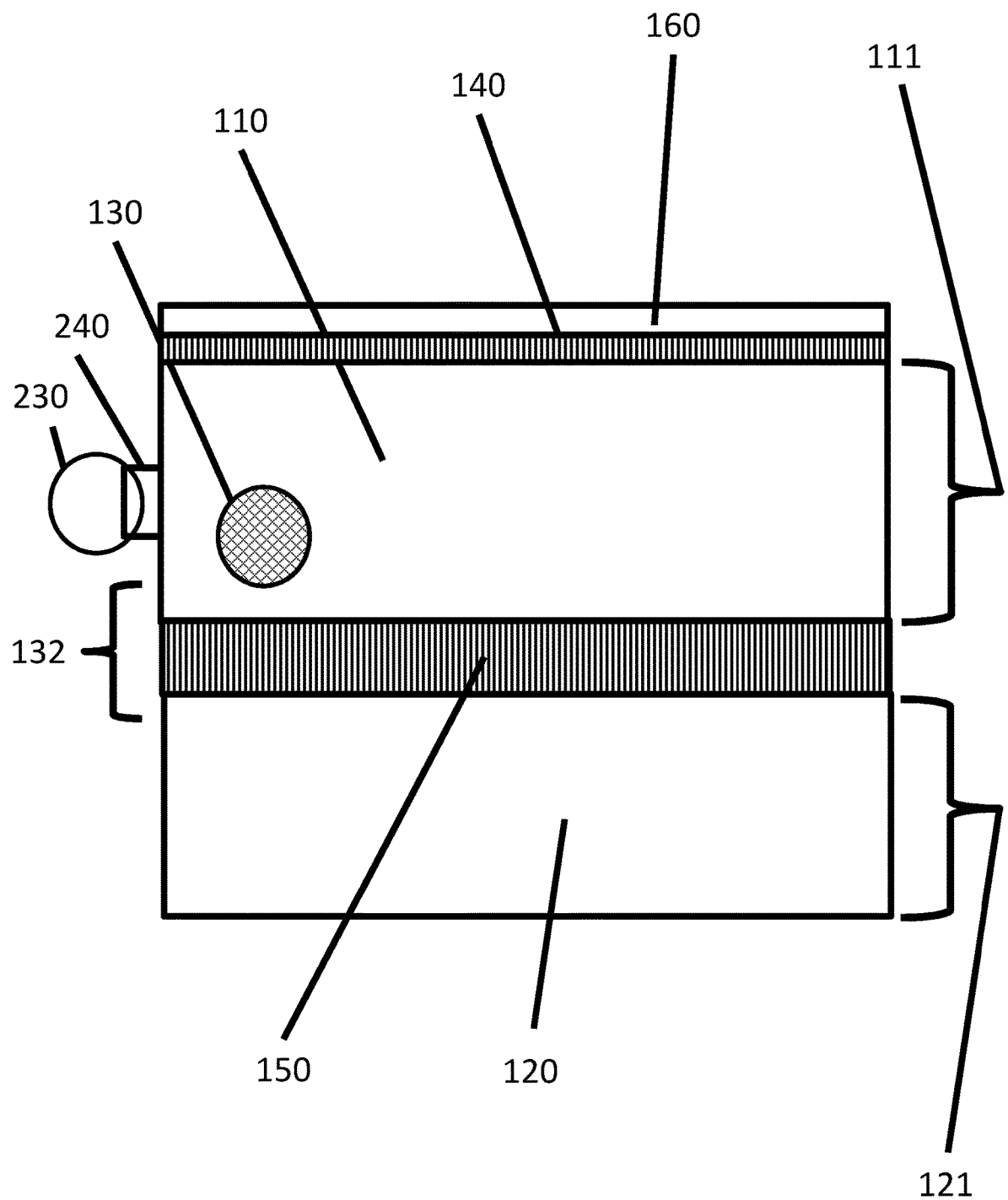
FIG. 7 shows a side perspective view of an automated external defibrillator soft carrying case.

FIG. 7 illustrates a side perspective view of an automated external defibrillator soft carrying case. As illustrated in FIG. 7, the automated external defibrillator soft carrying case is constructed of a first storage compartment 110 and a second storage compartment 120 with the accessibility to the first compartment 110 being enabled by using a zipper mechanism 140 and the accessibility to the second compartment 120 being enabled by using a zipper mechanism 150.

The first storage compartment 110 includes four walls formed by the outer walls of the automated external defibrillator soft carrying case and a floor. The second storage compartment 120 includes four walls formed by the outer walls of the automated external defibrillator soft carrying case and a floor. The floor of the first storage compartment 110 forms a ceiling for the second storage compartment 120.

The soft carrying case is constructed of a non-rigid material which includes padding material to prevent damage to the items contained within the soft carrying case.

For example, soft carrying case may be constructed of an outer shell of vinyl, leather, fabric, or non-rigid plastic material and an inner shell of vinyl, leather, fabric, or non-rigid plastic material with padding material sandwiched therebetween. It is noted that that the material of the outer shell and/or the material of the inner shell may be water proof or water resistant.

The first storage compartment 110 includes an audio window 130 at a hinged end (132) of the first compartment 110 to enable the transmission of the audio signals produced by an automated external defibrillator which would be located within the first compartment 110.

Figure 12:
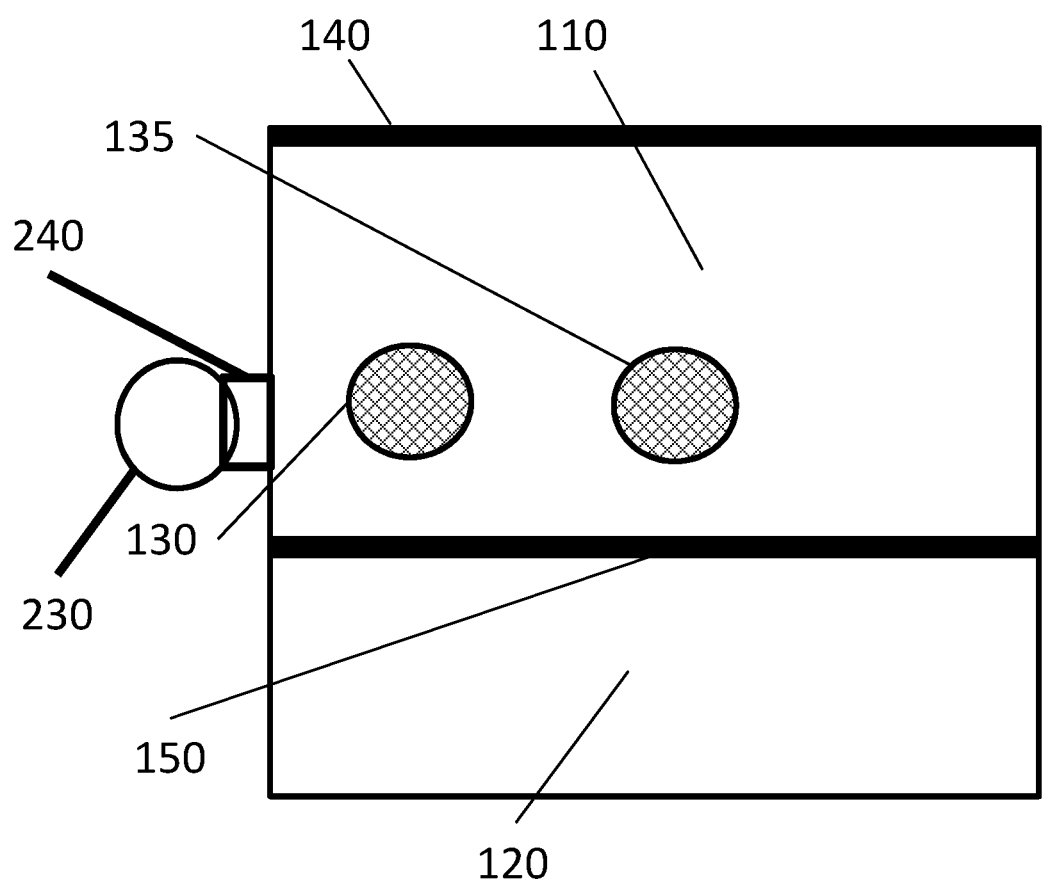
FIG. 12 shows a side perspective view of another embodiment of an automated external defibrillator soft carrying case with multiple audio windows.

It is noted that, as illustrated in FIG. 12, the first storage compartment 110 of the automated external defibrillator soft carrying case may include an additional audio window 135 at center of the first compartment 110 to enable the transmission of the audio signals produced by a differently configured automated external defibrillator which may be located within the first compartment 110.

Figure 13:
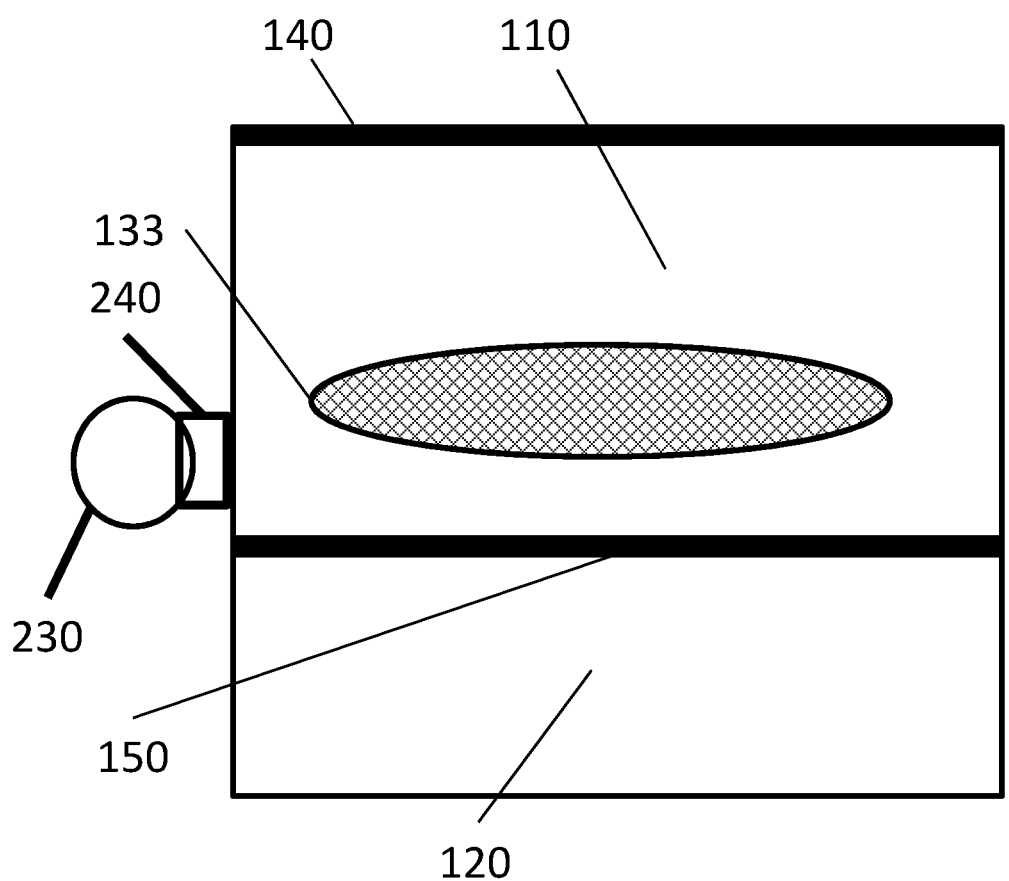
FIG. 13 shows a side perspective view of another embodiment of an automated external defibrillator soft carrying case with an elongated audio window.

Moreover, it is noted that, as illustrated in FIG. 13, the first storage compartment 110 of the automated external defibrillator soft carrying case may include an elongated audio window 133 to enable the transmission of the audio signals produced by a variety of differently configured automated external defibrillators which may be located within the first compartment 110.

The first compartment 110 of the automated external defibrillator soft carrying case includes a substantially flat cover 160, which forma a ceiling for the first compartment 110 of the automated external defibrillator soft carrying case. The first compartment 110 is accessible, through the flat cover 160, by using a zipper mechanism 140.

It is noted that the height 111 of the first compartment 110 is greater than the height 121 of the second compartment 120. The first compartment 110 of the automated external defibrillator soft carrying case includes a handle 240 and an attachment ring 230.

Figure 8:
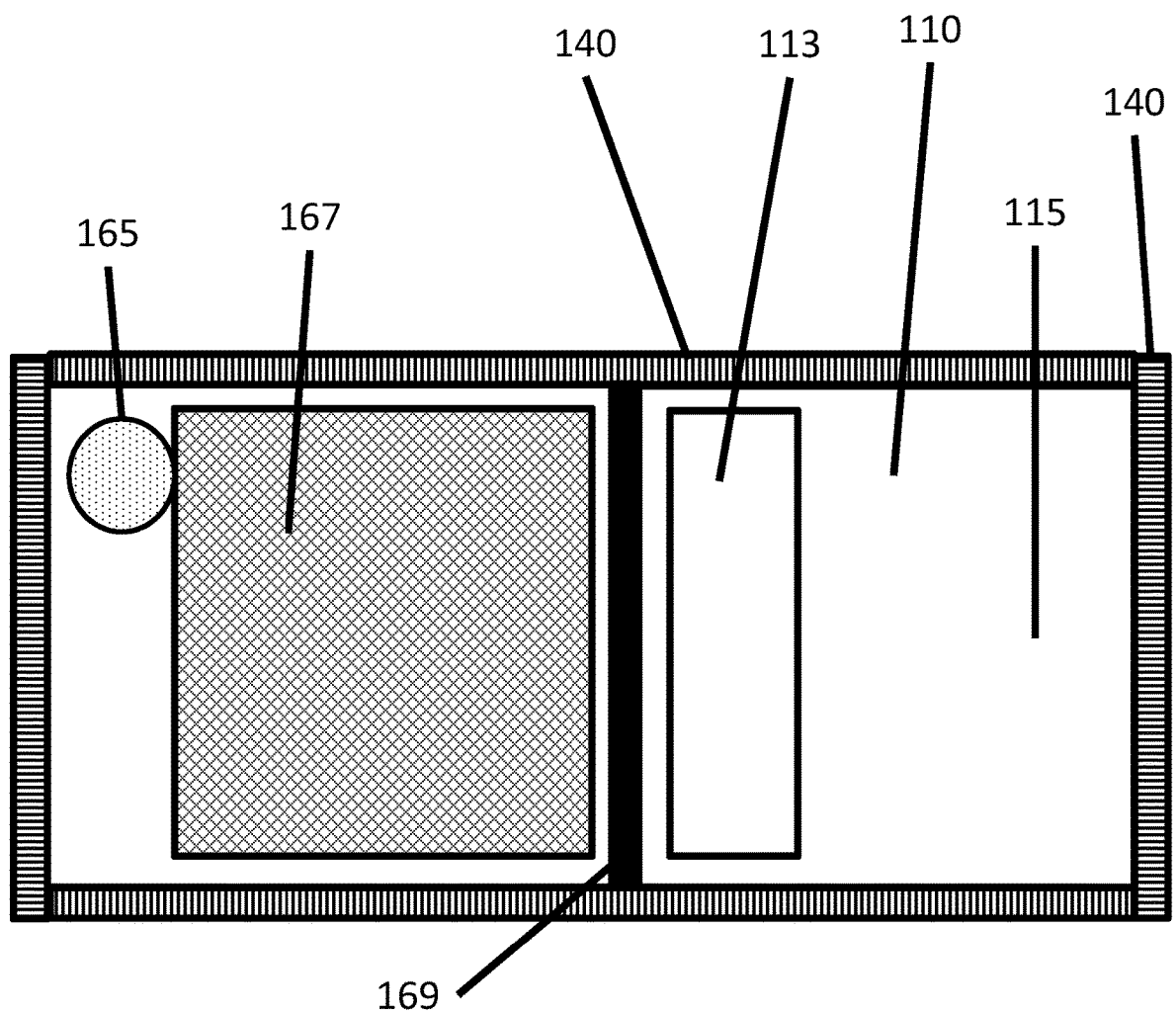
FIG. 8 shows a first compartment of the conventional automated external defibrillator soft carrying case of FIG. 7.

The first compartment 110 of the automated external defibrillator soft carrying case, as illustrated in FIG. 8, includes the cover 160 that has a securable storage pocket 167 located on an interior side of the cover 160 and a transparent window 165. The transparent window 165 allows the user to see the operational state of the enclosed automated external defibrillator without having to open the cover 160.

It is noted that the securable storage pocket 167 is a mechanism that allows the items to be secured in place or contained within a certain area or volume inside the first compartment 110 of the automated external defibrillator soft carrying case. It is further noted that the securable storage pocket 167 may be transparent.

The cover 160 is hinged (169) to a side wall of the first compartment 110. The hinge 169 may be the outer or inner shell (casing) of the automated external defibrillator soft carrying case.

The first compartment 110 of the automated external defibrillator soft carrying case, as illustrated in FIG. 8, includes a strap 113 or other mechanism for securing the automated external defibrillator in a proper position for operation while enclosed in the first compartment 110, and the first compartment 110 of the automated external defibrillator soft carrying case, as noted above, includes a floor 115.

Figure 11:
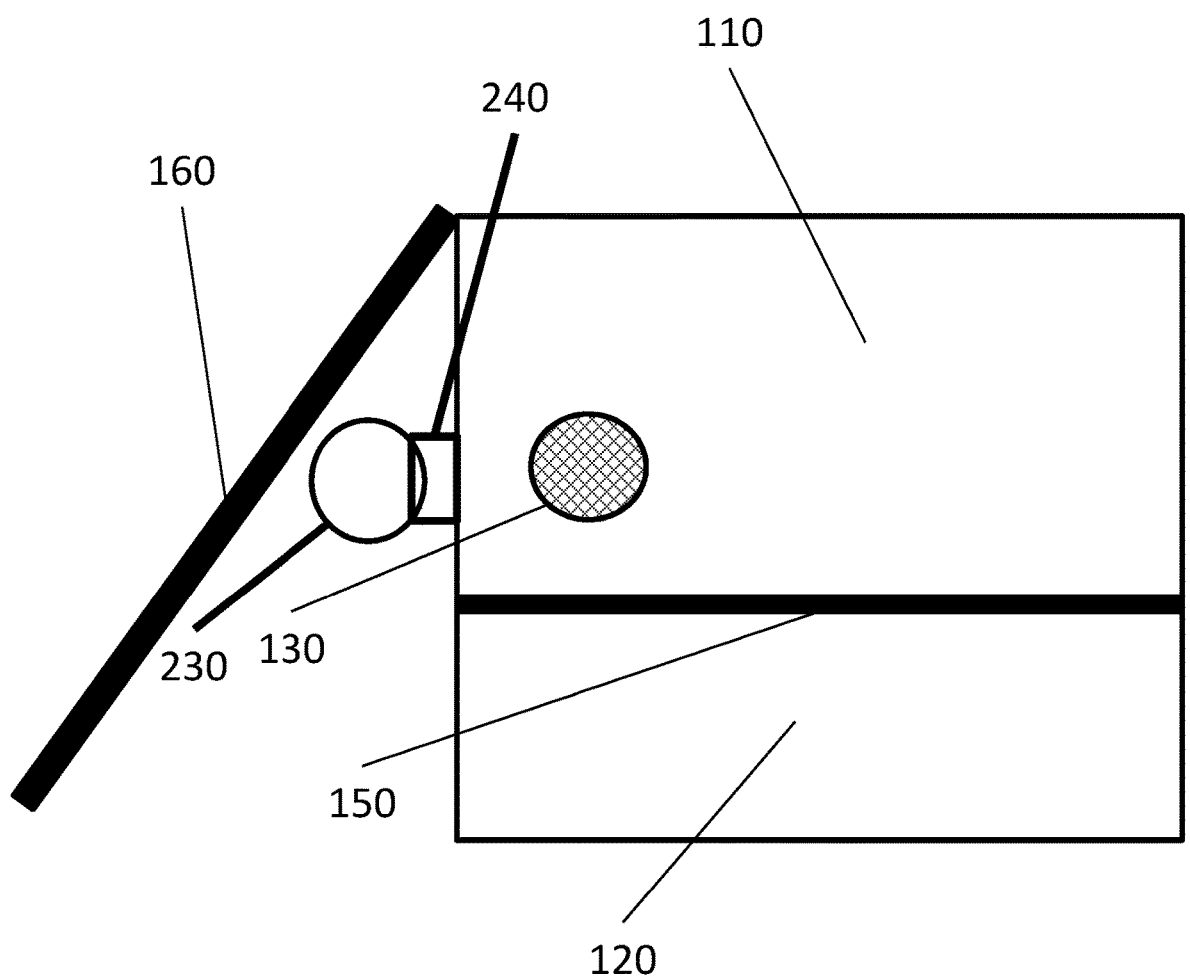
FIG. 11 illustrates the automated external defibrillator soft carrying case of FIG. 7 in a stable state when using or operating the automated external defibrillator while the automated external defibrillator is secured in the carrying case.

The weight of the cover 160 and the configuration of the hinge mechanism 169 being connected only to the cover 160 and the side wall of the first compartment 110 allow the first compartment 110 to be opened, through the flat cover 160, (allowing access to the automated external defibrillator located within the first compartment 110) without asserting forces on the automated external defibrillator soft carrying case, as illustrated in FIG. 11.

Figure 5:
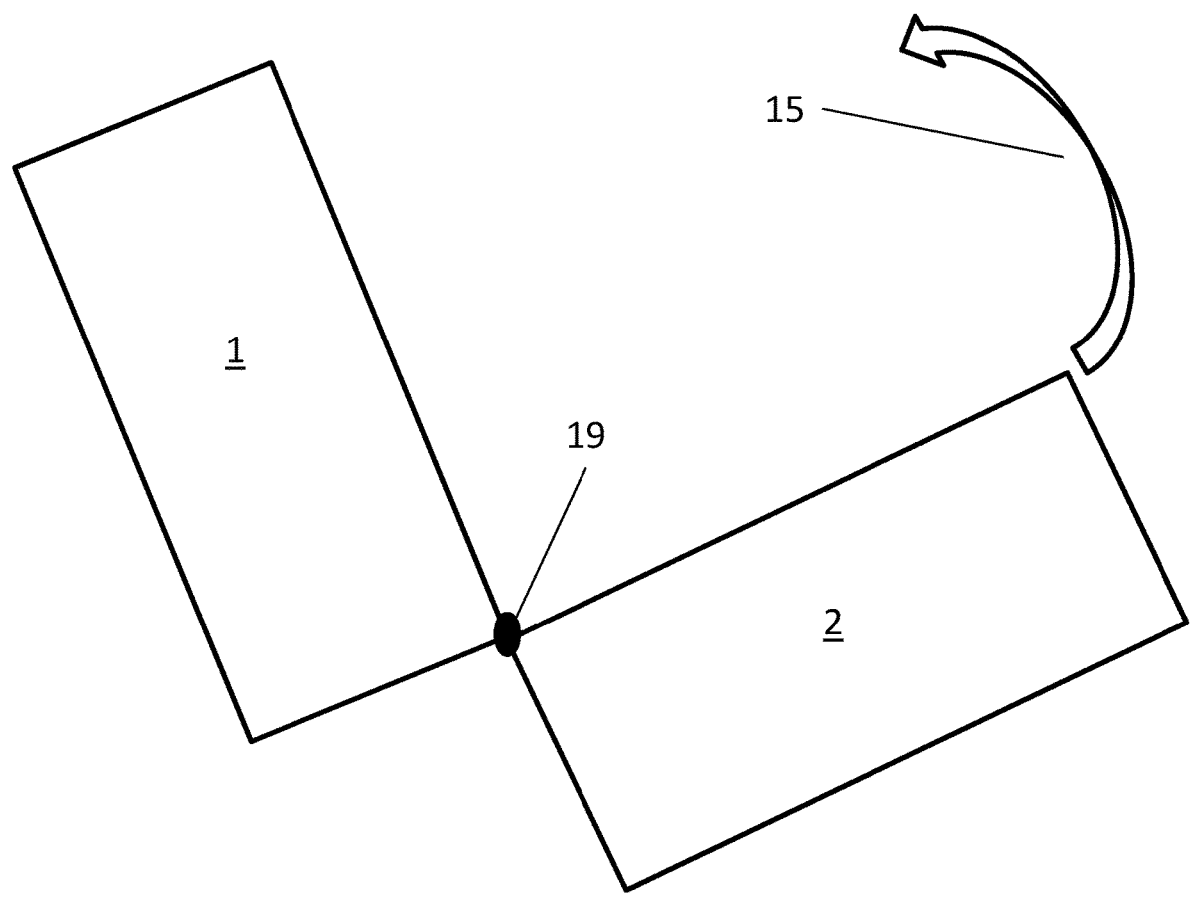
FIG. 5 illustrates a conventional automated external defibrillator soft carrying case tipping over.
Figure 6:
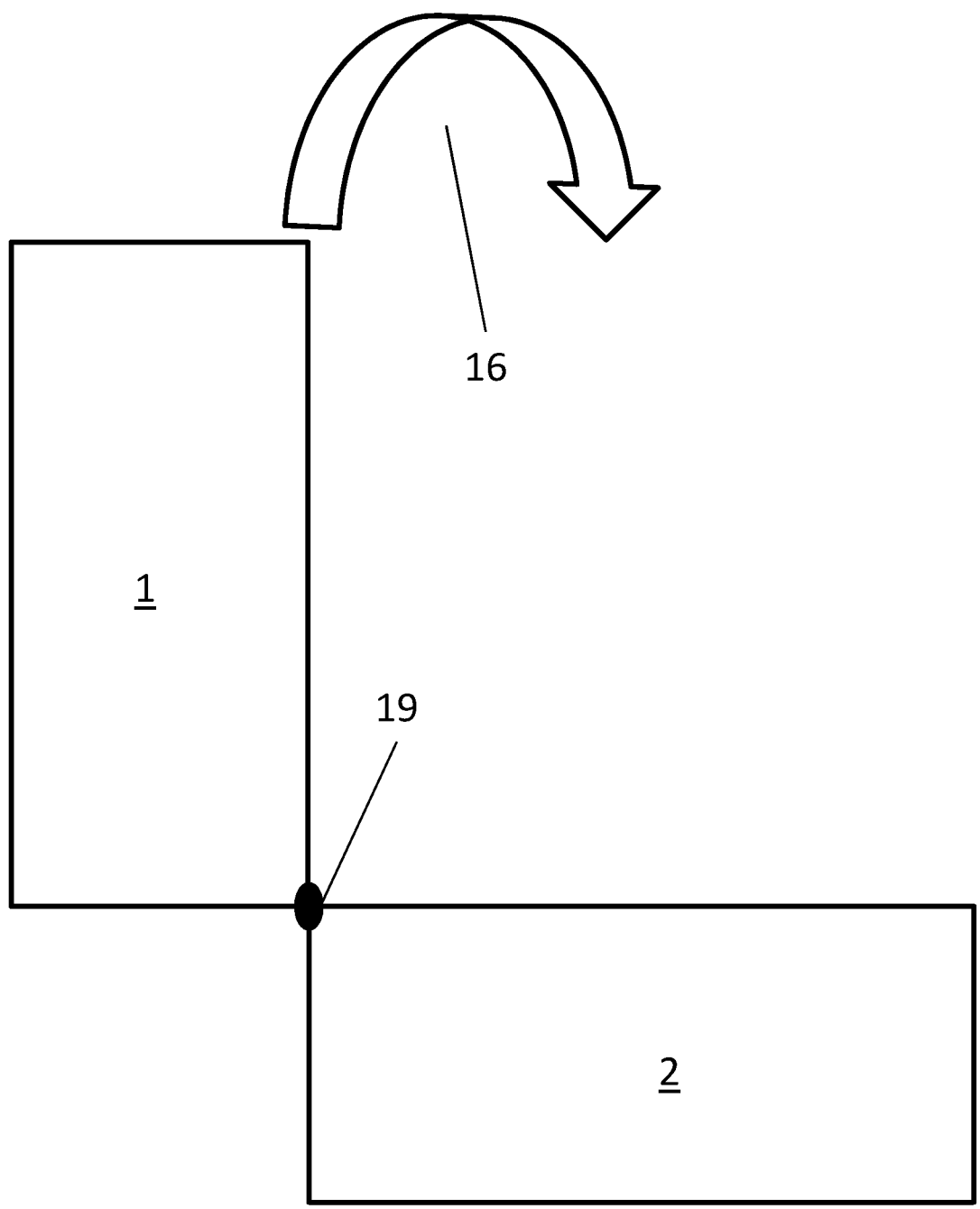
FIG. 6 shows a first compartment conventional automated external defibrillator soft carrying case closing upon the second compartment.

In other words, the opening of the first compartment 110 will not cause the automated external defibrillator soft carrying case to tip over as the conventional automated external defibrillator soft carrying cases experience, as illustrated in FIG. 5.

Figure 9:
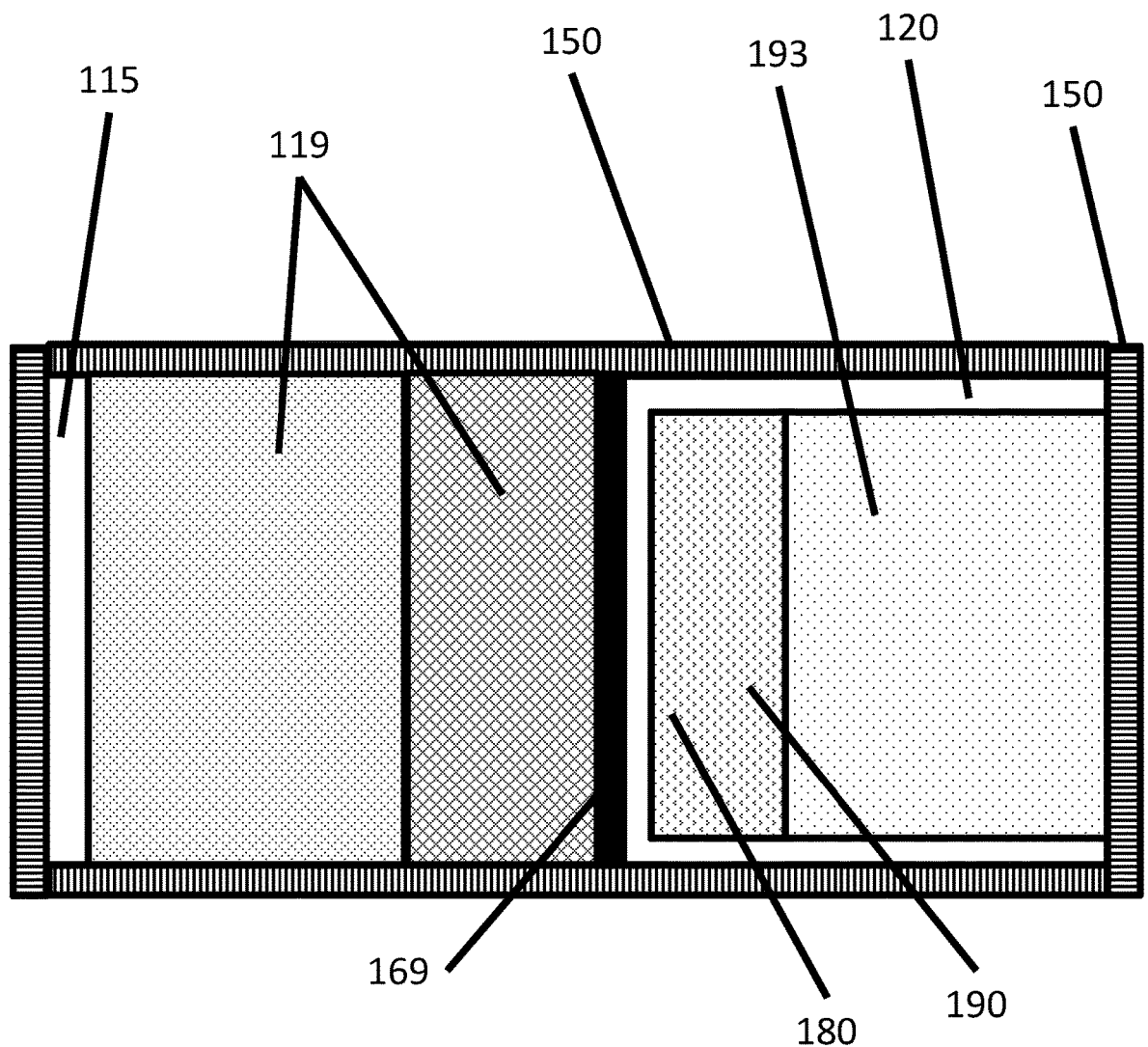
FIG. 9 shows a second compartment of the conventional automated external defibrillator soft carrying case of FIG. 7.

The second compartment 120 of the automated external defibrillator soft carrying case, as illustrated in FIG. 9, includes securable storage pockets 119 located on a backside side of the floor 115 of the first compartment 110, wherein the backside side of the floor 115 is located on an opposite side of the floor 115 that is within the first compartment 110, as illustrated in FIG. 8. It is noted that the securable storage pockets 119 may be transparent.

The second compartment 120 of the automated external defibrillator soft carrying case, as illustrated in FIG. 9, also includes a removable false floor (ceiling) or divider 190 having a securable storage pocket 193 thereon. The removable false floor (ceiling) or divider 190 is detachably attached to a side wall of the second compartment 120 by an attachment mechanism 180. It is noted that the securable storage pocket 193 may be transparent.

It is noted that multiple removable false floors or dividers may be attached with the attachment mechanism. It is further noted that the attachment mechanism 180 should allow easy detachment by a pulling or ripping motion (e.g., Velcro™), thereby allowing quick access to the medical items in the securable storage areas.

Figure 10:
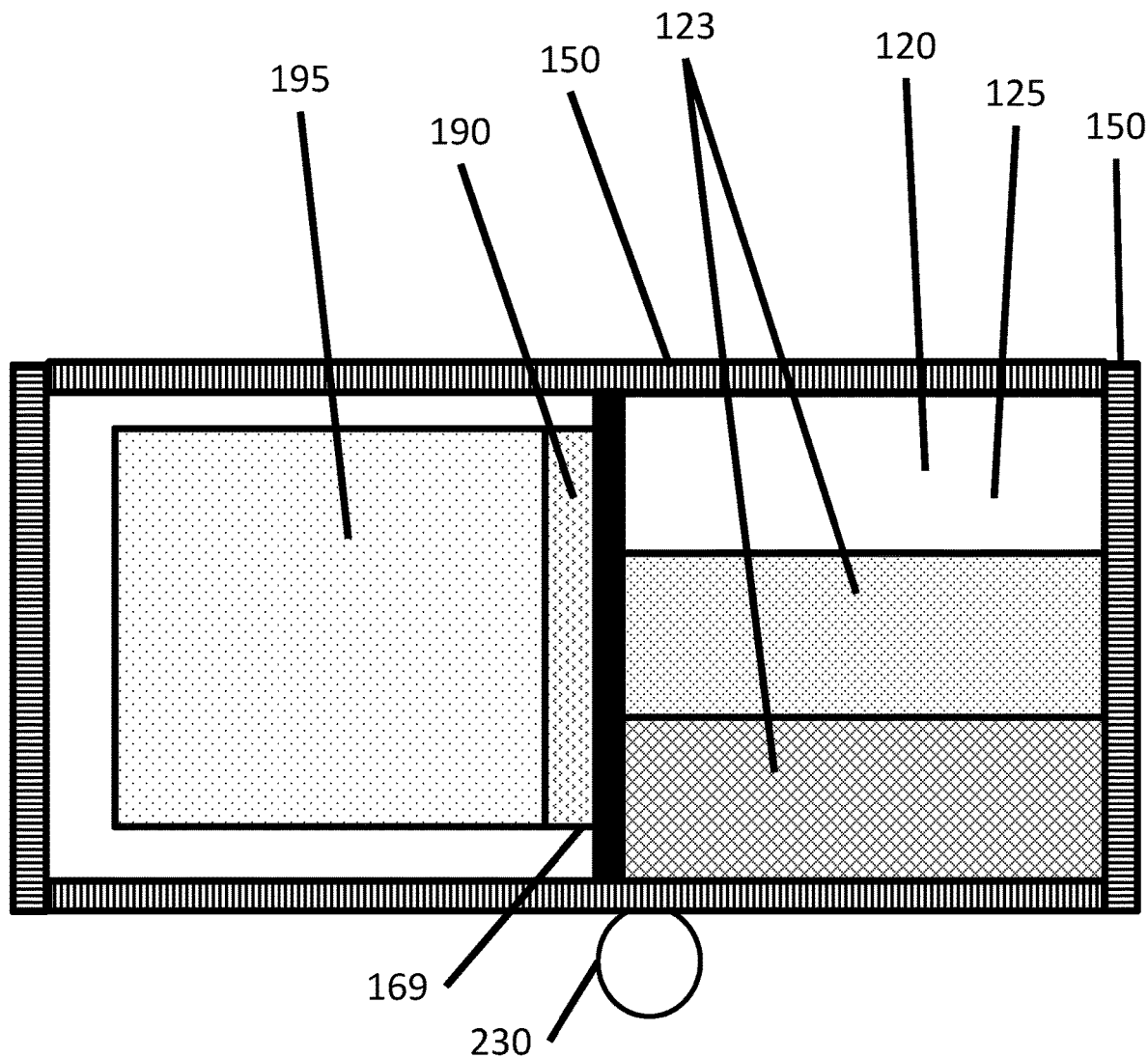
FIG. 10 shows another perspective of the second compartment of the conventional automated external defibrillator soft carrying case of FIG. 7.

As illustrated in FIG. 9, the second compartment 120 is accessible by opening the zipper mechanism 150 and moving the first compartment 110 through a hinge mechanism 169. The hinge mechanism 169 is connected to floor/sidewall of the first compartment 110 and a sidewall of the second compartment 120. The area of the second compartment 120 of the automated external defibrillator soft carrying case below the removable false floor or divider 190, as illustrated in FIG. 10, includes securable storage pockets 123, and the second compartment 120 of the automated external defibrillator soft carrying case includes a floor 121. It is noted that the securable storage pockets 123 may be transparent.

The removable false floor or divider 190 includes a securable storage pocket 195 on the side opposing the securable storage pockets 123 on the floor 121 of the second compartment 120. It is noted that the securable storage pocket 195 may be transparent.

Figure 14:
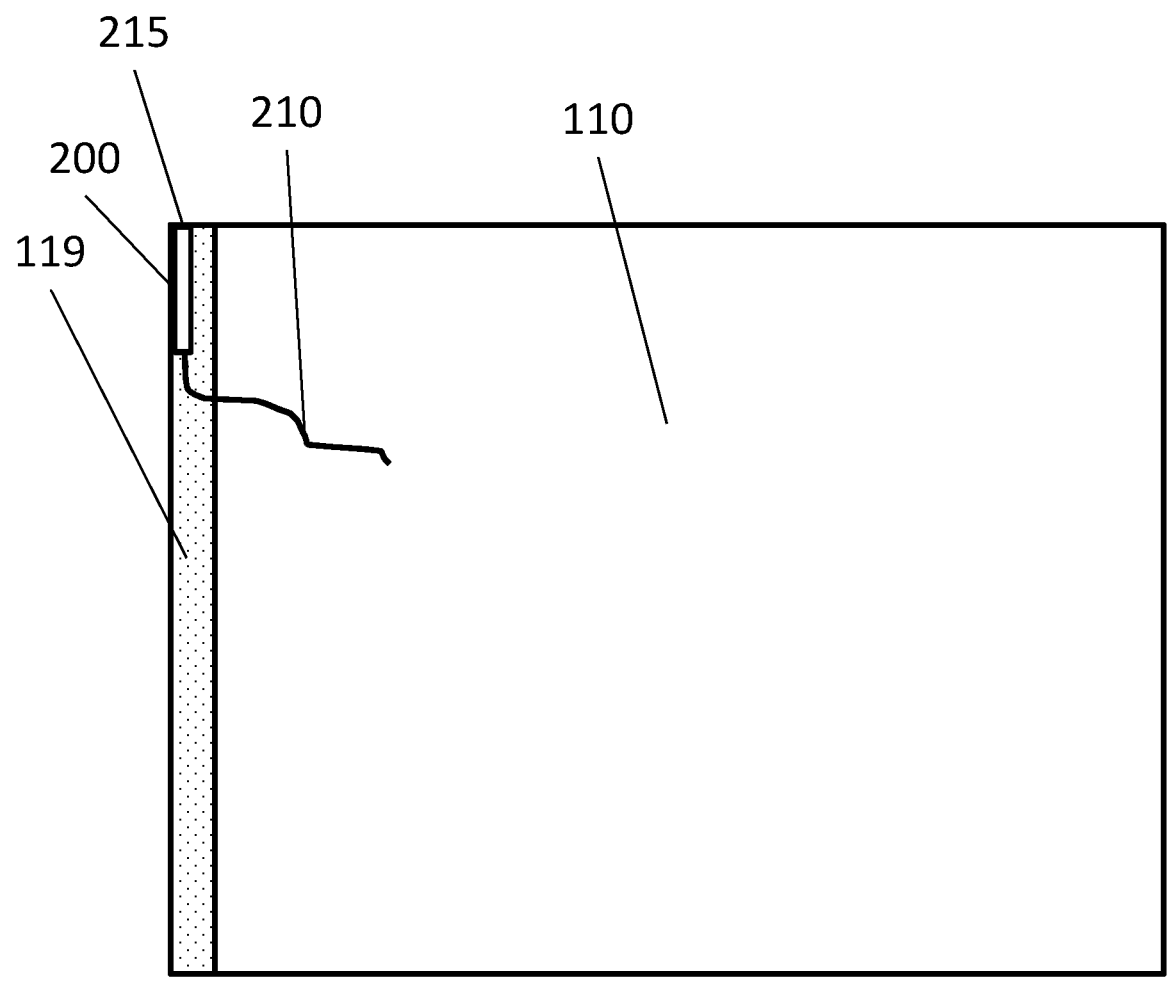
FIG. 14 shows another embodiment of an automated external defibrillator soft carrying case with charging port for the automated external defibrillator.

FIG. 14 illustrates a top view of the first storage compartment 110 of the automated external defibrillator soft carrying case with the flat cover 160 removed for illustrative purposes, wherein the first storage compartment 110 includes a side wall 119. As illustrated in FIG. 14, within the side wall 119, a power receptacle 200 is located such that the power receptacle 200 is parallel to a planar outer surface of the side wall 119.

In addition, the power receptacle 200 may include a plug device 215, which protects the power receptacle 200 from debris (such as dust or dirt) and/or fluids (such as water.) The plug device 215 may be tethered to the automated external defibrillator soft carrying case to prevent the plug device 215 from being lost or misplaced.

By having the power receptacle 200 parallel to the planar outer surface of the side wall 119, the power receptacle 200 will not interfere with the automated external defibrillator located in the first storage compartment 110.

It is noted that the power receptacle 200 may, alternatively, be located in the cover 160 of the automated external defibrillator soft carrying case, wherein the power receptacle 200, within the cover 160 of the automated external defibrillator soft carrying case, is parallel to a planar outer surface of the cover 160 so that the power receptacle 200 will not interfere with the automated external defibrillator located in the first storage compartment 110.

It is noted that the power receptacle 200 may, alternatively, be located in the divider (floor 115 of the first storage compartment 110) between the first storage compartment 110 of the automated external defibrillator soft carrying case and the second storage compartment 120 of the automated external defibrillator soft carrying case, wherein the power receptacle 200, within the floor 115 of the first storage compartment 110, is parallel to a planar outer surface of the floor 115 of the first storage compartment 110 so that the power receptacle 200 will not interfere with the automated external defibrillator located in the first storage compartment 110.

The power receptacle 200 is connected to an electrical cord 210, which connects to the automated external defibrillator located in the first storage compartment 110. This allows the automated external defibrillator to be recharged while the automated external defibrillator is located in the first storage compartment 110.

Moreover, the combination of the power receptacle 200 and the electrical cord 210 may be used to power or charge any electrical device located within the first storage compartment 110, the second storage compartment 120, or the automated external defibrillator soft carrying case.

For example, the combination of the power receptacle 200 and the electrical cord 210 may be used to power a heating element located within the first storage compartment 110, the second storage compartment 120, or the automated external defibrillator soft carrying case.

Figure 15:
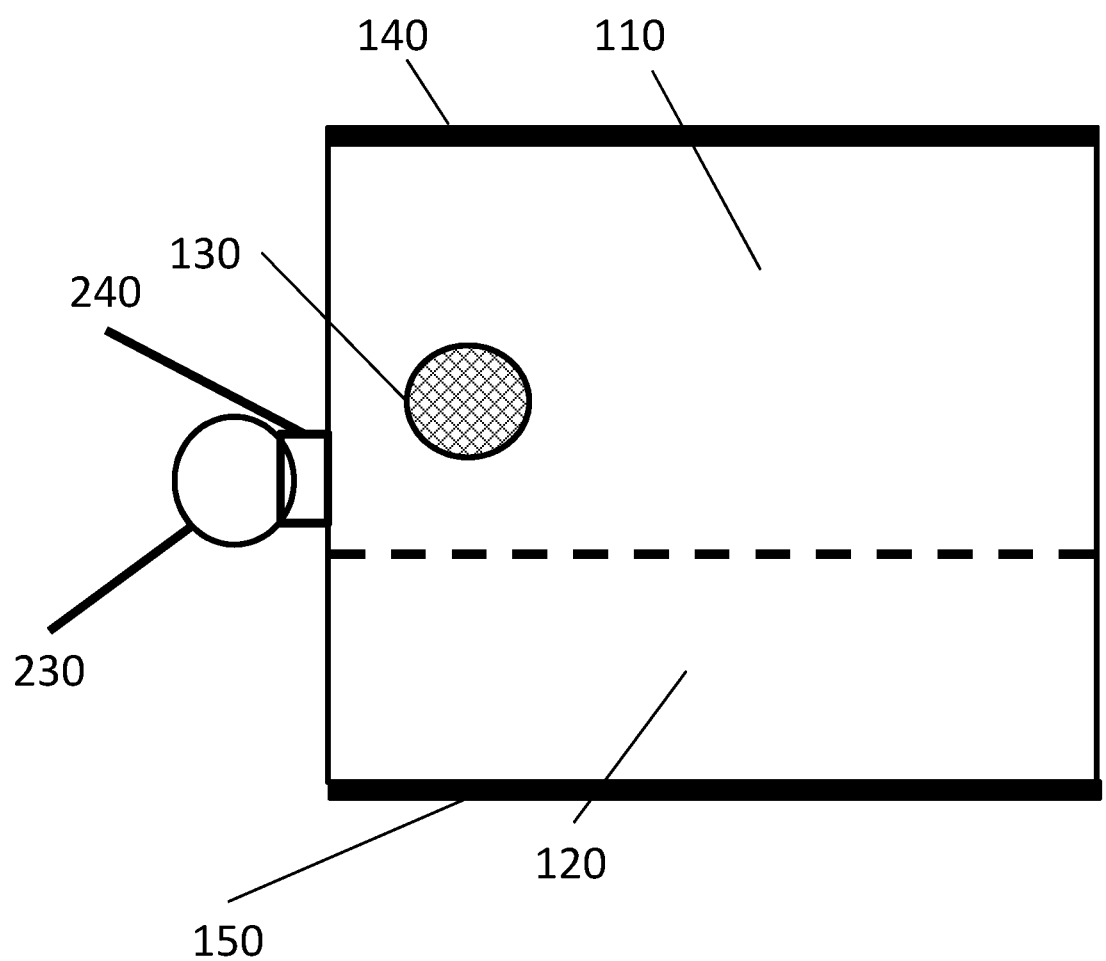
FIG. 15 shows another embodiment of an automated external defibrillator soft carrying case.

As illustrated in FIG. 15, another embodiment of the automated external defibrillator soft carrying case may be constructed so that the first compartment 110 is accessed via a zipper mechanism 140 without moving the second compartment 120.

In the embodiment of FIG. 15, the second compartment 120 is accessed via a zipper mechanism 150 without moving the first compartment 110. More specifically, the compartments are accessed via independent covers that are on opposite sides of the automated external defibrillator soft carrying case.

Figure 16:
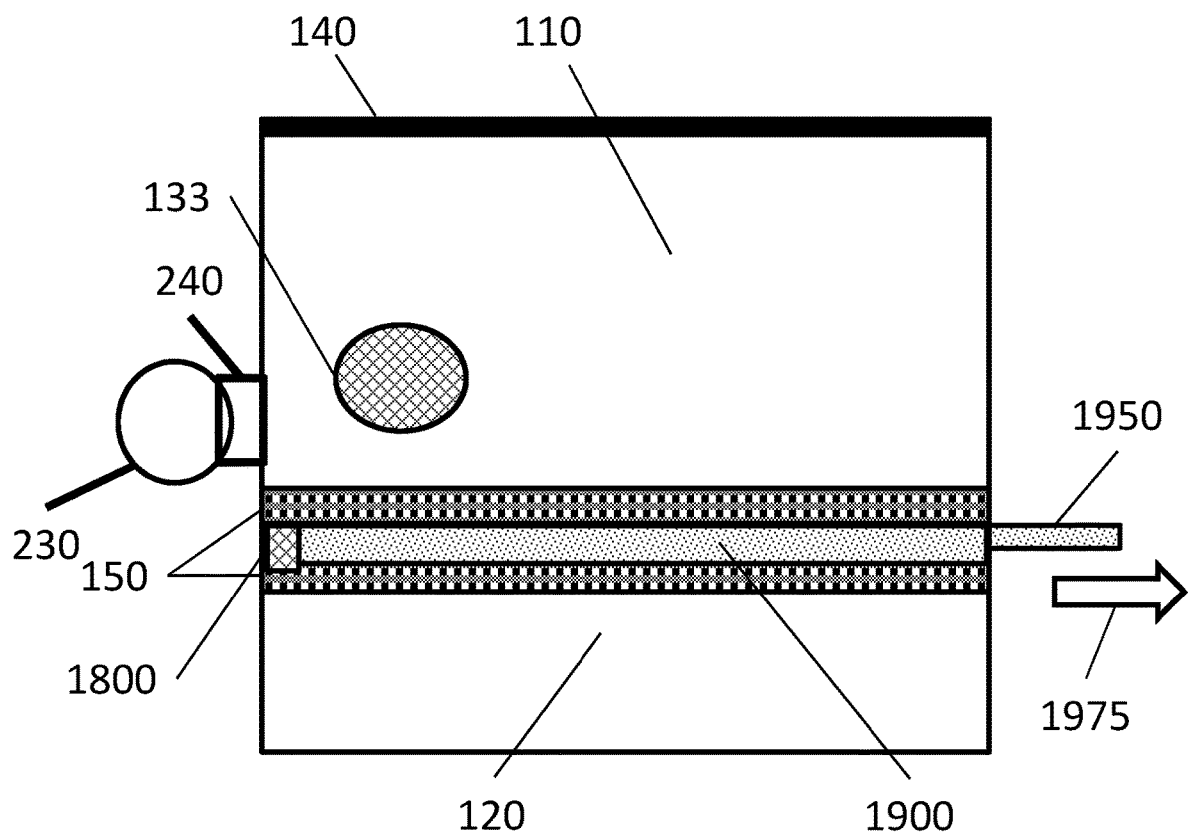
FIG. 16 shows a side view of another embodiment of an automated external defibrillator soft carrying case with a tear away electrode pad storage container.
Figure 17:
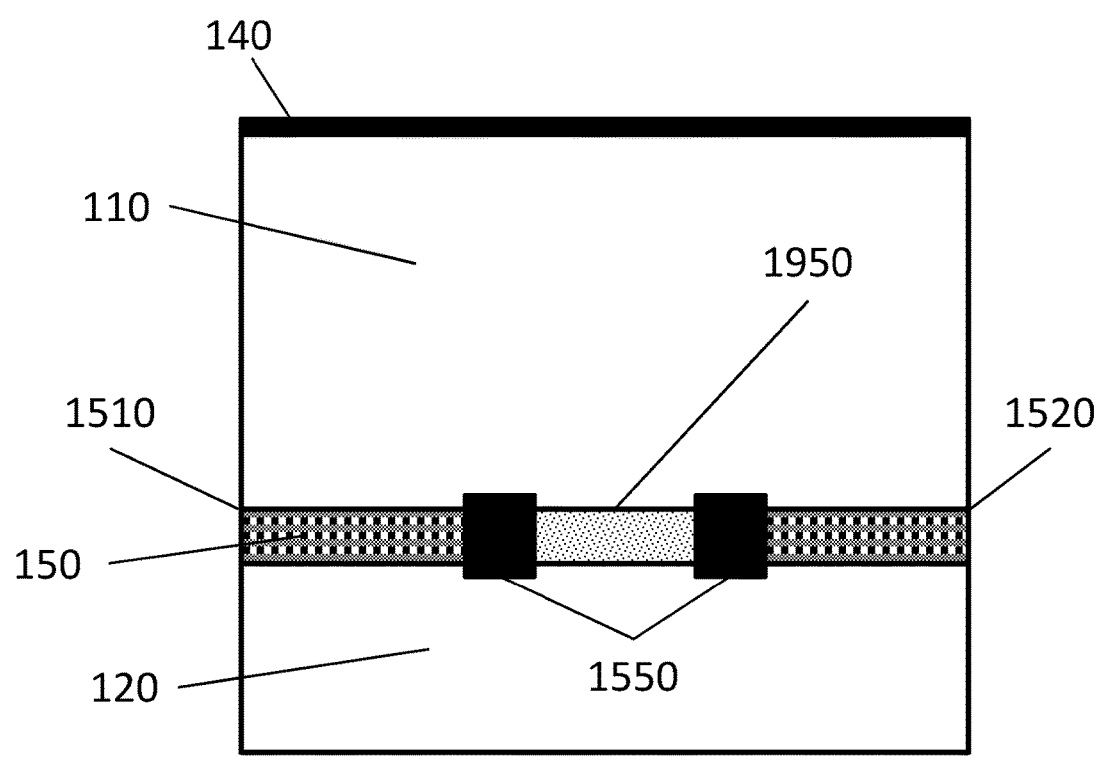
FIG. 17 shows a front view of the embodiment of FIG. 16 with the tear away electrode pad storage container.

FIGS. 16 and 17 illustrate an embodiment of the automated external defibrillator soft carrying case, wherein the removable false floor or divider 190 of FIGS. 9 and 10 can be readily accessed without fully opening the second compartment 120.

As illustrated in FIG. 16, an automated external defibrillator soft carrying case includes a first compartment 110, which is accessible via zipper mechanism 140. The first compartment 110 includes an audio window 133. The automated external defibrillator soft carrying case also includes a second compartment 120, which is accessible via zipper mechanism 150. The second compartment 120 includes a removable false floor or divider 1900.

The removable false floor or divider 1900 includes a handle 1950, which projects out from the second compartment 120. The handle 1950 provides, to a user, a mechanism to grasp for pulling (in the direction 1975) the removable false floor or divider 1900 from the second compartment 120.

As previously noted, the removable false floor or divider 1900 is detachably attached to a side wall of the second compartment 120 by an attachment mechanism 1800.

It is noted that the attachment mechanism 1800 should allow easy detachment by a pulling or ripping motion (e.g., Velcro™), thereby allowing quick access to the medical items in the securable storage areas.

In this embodiment, the medical items in the securable storage areas would include electrode pads, gel for the electrode pads, a face shield, a pair of nitrile rubber gloves, shears, cleaning cloth, and/or a razor; i.e., items that would be utilized with the automated external defibrillator.

As illustrated in FIG. 16, pulling the handle 1950 in the direction 1975 will cause the removable false floor or divider 1900 to disengage from the attachment mechanism 1800. Continual pulling of the handle 1950 in the direction 1975 will cause the removable false floor or divider 1900 to exit the second compartment 120.

For illustrative purposes, FIG. 16 illustrates the removable false floor or divider 1900 and the attachment mechanism 1800. However, in most situations, the removable false floor or divider 1900 and the attachment mechanism 1800 would not be visible as the zipper mechanism 150 would be in a closed state, thereby bringing the two sets of teeth together.

FIG. 17 illustrates a front view of the embodiment of FIG. 16. As illustrated in FIG. 17, the second compartment 120 of the automated external defibrillator soft carrying case is in a closed state, wherein the zipper sliders 1550 of the zipper mechanism 150 are positioned adjacent to the projecting handle 1950.

When a user desires to remove the removable false floor or divider 1900 from the second compartment 120 of the automated external defibrillator soft carrying case, the user initially moves the zipper sliders 1550 of the zipper mechanism 150 to a position that is located approximately at the front corners (1510 and 1520) of the second compartment 120 of the automated external defibrillator soft carrying case. This allows the teeth of the zipper mechanism 150 to disengage, creating an opening for the removal of the remove the removable false floor or divider 1900 from the second compartment 120 of the automated external defibrillator soft carrying case.

The embodiment of FIGS. 16 and 17 enables a user to quickly acquire the items needed to operate the automated external defibrillator without fully opening the second compartment 120 of the automated external defibrillator soft carrying case.

Figure 18:
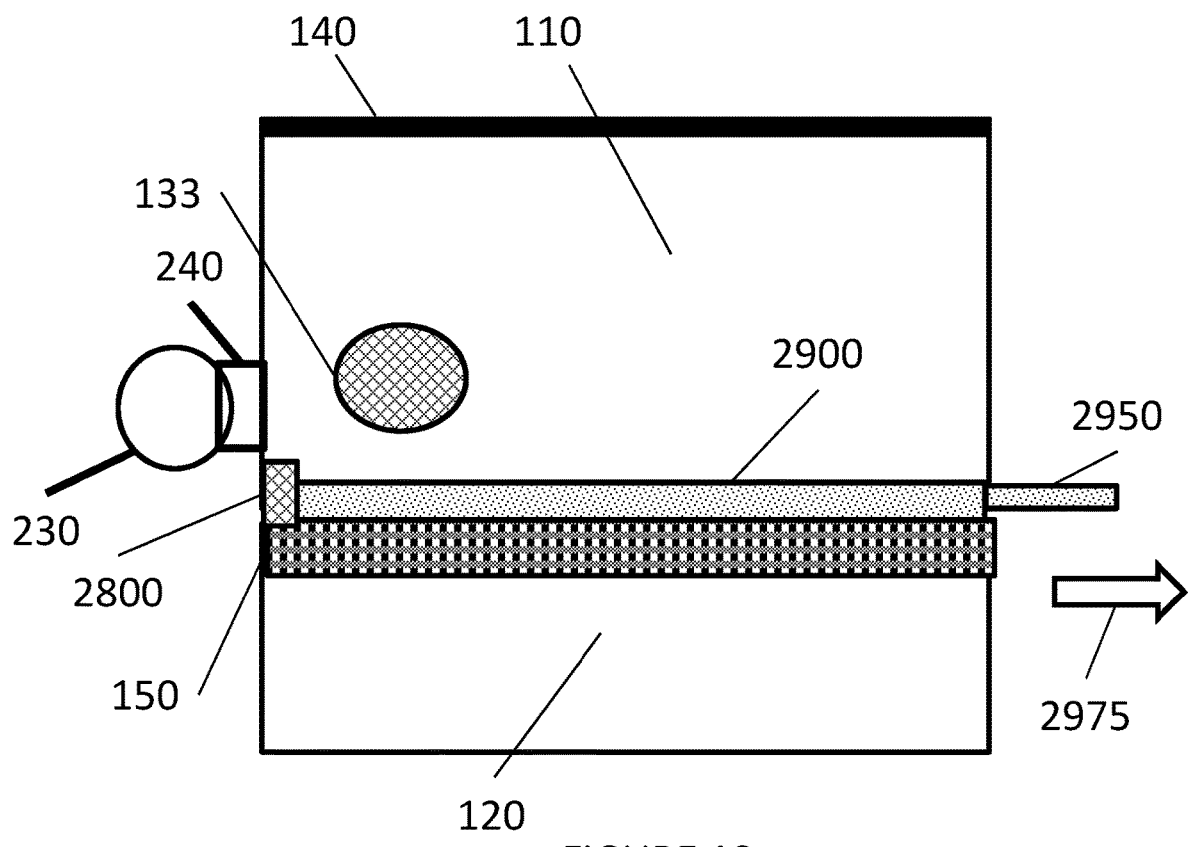
FIG. 18 shows a side view of another embodiment of an automated external defibrillator soft carrying case with a tear away electrode pad storage container.
Figure 19:
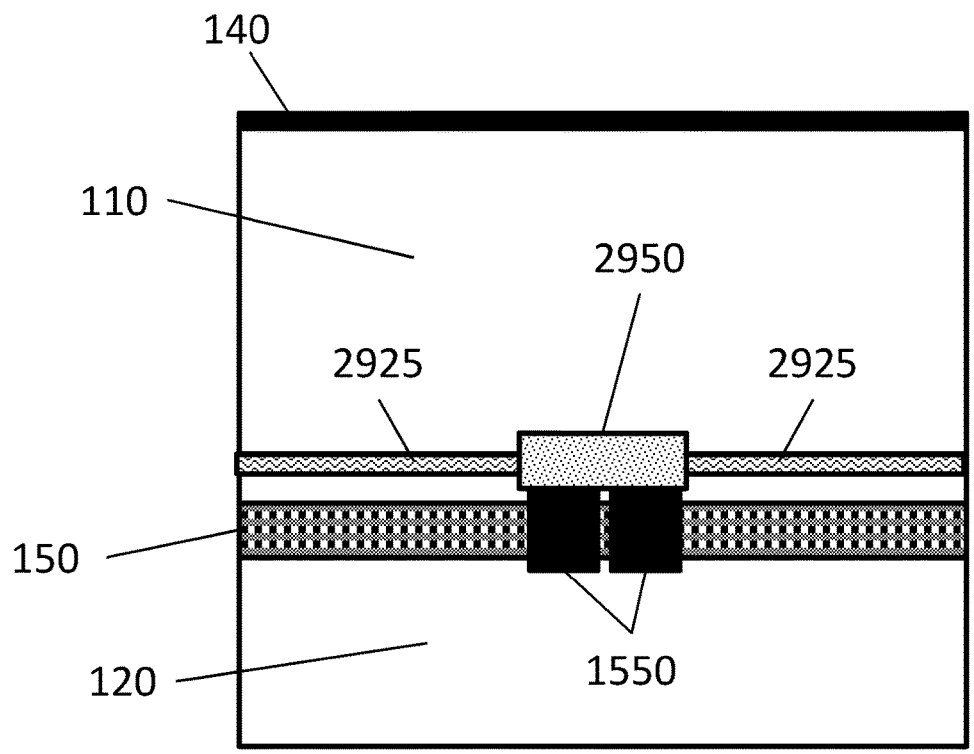
FIG. 19 shows a front view of the embodiment of FIG. 18 with the tear away electrode pad storage container.

FIGS. 18 and 19 illustrate another embodiment of the automated external defibrillator soft carrying case, wherein a movable or removable false floor 2900 located between the first compartment 110 and the second compartment 120, which can be readily accessed without opening either the first compartment 110 or the second compartment 120.

As illustrated in FIG. 18, an automated external defibrillator soft carrying case includes a first compartment 110, which is accessible via zipper mechanism 140. The first compartment 110 includes an automated external defibrillator and an audio window 133. The automated external defibrillator soft carrying case also includes a second compartment 120, which is accessible via zipper mechanism 150.

The removable false floor or panel 2900 includes a handle 2950, which projects out from the first compartment 110, above the zipper mechanism 150. The handle 2950 provides, to a user, a mechanism to grasp for pulling the removable false floor or panel 2900 from the automated external defibrillator soft carrying case.

It is noted that the removable false floor or panel 2900 may be detachably attached to a side wall of the automated external defibrillator soft carrying case by an attachment mechanism 2800. It is further noted that the attachment mechanism 2800 should allow easy detachment by a pulling or ripping motion (e.g., Velcro™), thereby allowing quick access to the medical items (e.g., electrode pads) associated with the removable false floor or panel 2900.

In this embodiment, the medical items may include electrode pads, which are pre-connected to the automated external defibrillator, such that when the removable false floor or panel 2900 is pulled away from the of the first compartment 110, the electrode pads pre-connected to the automated external defibrillator become accessible for utilization by the user of the automated external defibrillator.

As illustrated in FIG. 18, pulling the handle 2950 in the direction 2975 will cause the removable false floor or panel 2900 to disengage from the optional attachment mechanism 2800. Continual pulling of the handle 2950 in the direction 2975 will cause the removable false floor or panel 2900 to partially or completely exit the first compartment 110, thereby providing accessibility to the electrode pads pre-connected to the automated external defibrillator.

FIG. 19 illustrates a front view of the embodiment of FIG. 18. As illustrated in FIG. 19, the second compartment 120 of the automated external defibrillator soft carrying case is in a closed state, wherein the zipper sliders 1550 of the zipper mechanism 150 are positioned adjacent to each other.

When a user desires to remove the removable false floor or panel 2900 from the automated external defibrillator soft carrying case, the user will pull upon the handle 2950 of the movable or removable false floor 2900. This will cause the movable or removable false floor 2900 to move outwardly from the drawing and through a slit mechanism 2925.

The slit mechanism 2925 is biased to a closed state to protect the automated external defibrillator within the first compartment 110 of the automated external defibrillator soft carrying case from debris (such as dust or dirt) and/or fluids (such as water.)

However, the slit mechanism 2925 is weak enough to allow an opening to be created when the user pulls upon the handle 2950 of the removable false floor or panel 2900 so that the removable false floor or panel 2900 can move therethrough.

The embodiment of FIGS. 18 and 19 enables a user to quickly acquire the items (electrode pads) needed to operate the automated external defibrillator without opening the second compartment 120 of the automated external defibrillator soft carrying case.

Figure 20:
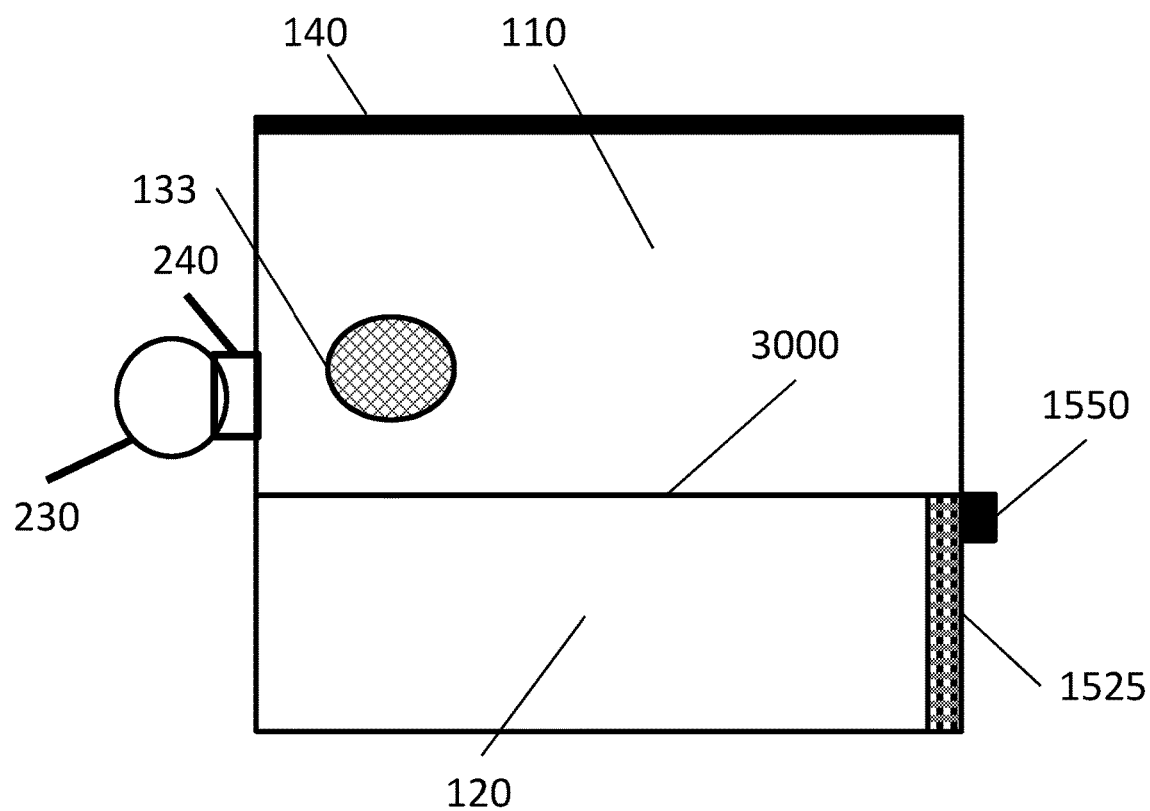
FIG. 20 shows a side view of another embodiment of an automated external defibrillator carrying case with a side flap cover for the second compartment.
Figure 21:
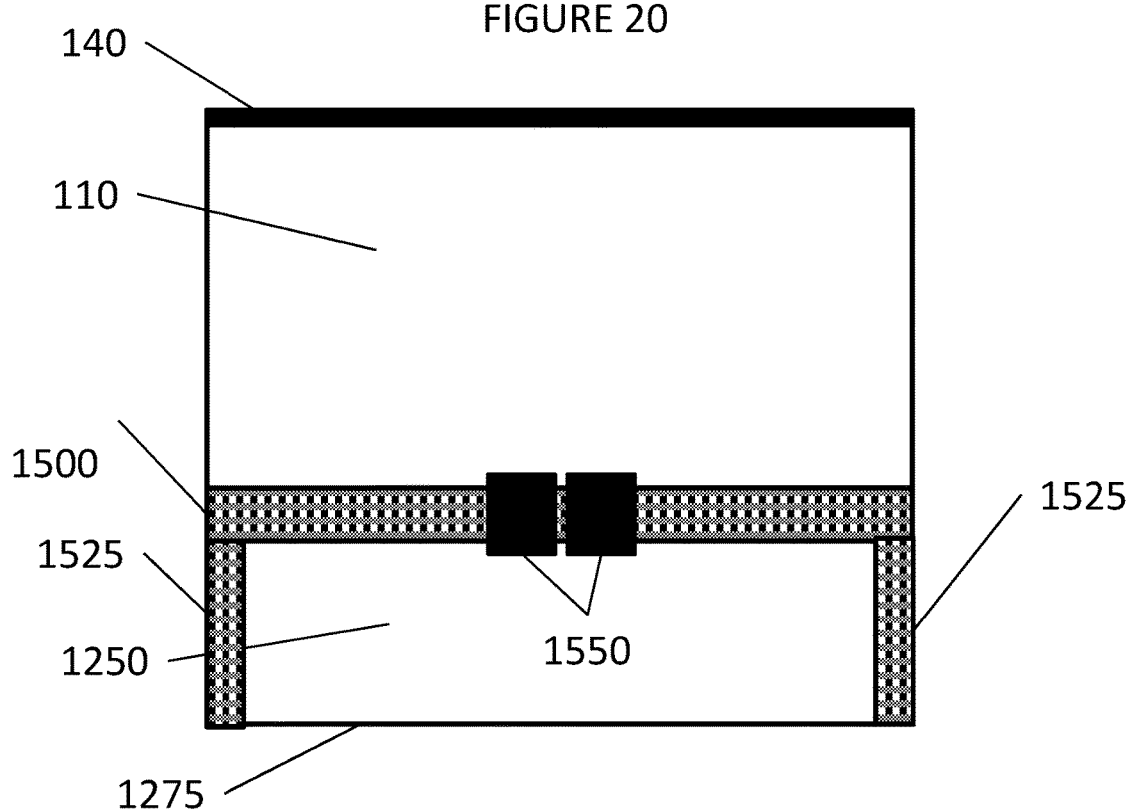
FIG. 21 shows s front view of the embodiment of FIG. 20.

FIGS. 20 and 21 illustrate another embodiment of the automated external defibrillator carrying case, wherein a cover 1250, located on a side of the second compartment 120, can be readily disengaged to enable access to the contents within the second compartment 120 without disengaging to other side walls of the second compartment 120 from the first compartment 110.

As illustrated in FIG. 20, an automated external defibrillator carrying case includes a first compartment 110, which is accessible (through a cover not shown) via zipper mechanism 140. The first compartment 110 may include an automated external defibrillator and an audio window 133. The automated external defibrillator carrying case also includes a second compartment 120, which is accessible via zipper mechanism 1525, using zipper slider 1550. A floor or panel 3000 is located between the first compartment 110 and the second compartment 120.

FIG. 21 illustrates a front view of the embodiment of FIG. 20. As illustrated in FIG. 21, the second compartment 120 of the automated external defibrillator carrying case is in a closed state, wherein the zipper sliders 1550 of the zipper mechanisms (1500 and 1525) are positioned adjacent to each other. It is noted that zipper mechanisms (1500 and 1525) create a single zipper mechanism wherein one zipper mechanism is substantially orthogonal to the remaining two zipper mechanisms.

When a user desires to access the second compartment, the user moves the zipper sliders 1550 to disengage the teeth of the zipper mechanisms (1500 and 1525). This will cause the cover 1250 to disengage from the second compartment, creating an opening into the second compartment.

It is noted that the cover 1250 remains partially engaged to the second compartment via the hinge mechanism 1275.

The embodiment of FIGS. 20 and 21 enables a user to quickly acquire the items stored in the second compartment 120 without opening the second compartment 120 of the automated external defibrillator carrying case from the top.

It is noted that, in an alternative embodiment, the cover 1250 may be a soft wall of the second compartment 120.

It is further noted that the remaining side walls of the second compartment of the alternative embodiment discussed above with respect to FIGS. 20 and 21 may be rigid or semi-rigid to provide a stable base for the first compartment when the contents of the second compartment are removed.

Alternatively, it is noted that the cover 1250 of the second compartment of the embodiment illustrated in FIGS. 20 and 21 may be a rigid or semi-rigid wall of the second compartment 120.

It is further noted that the remaining side walls of the second compartment of the alternative embodiment discussed above with respect to FIGS. 20 and 21 may be rigid or semi-rigid to provide a stable base for the first compartment when the contents of the second compartment are removed.

It is noted that although the various illustrations show multiple zipper slides for the zipper mechanism, a single zipper slide can be utilized to operate the zipper mechanism.

In summary, an automated external defibrillator soft carrying case, comprises a first compartment having first, second, third, and fourth compartment walls and a first compartment floor; and a second compartment having first, second, third, and fourth second compartment walls and a first compartment floor; the first compartment wall of the first compartment being connected to the first compartment wall of the second compartment by a first hinge mechanism; the second compartment wall of the first compartment being detachably connected to the second compartment wall of the second compartment; the third compartment wall of the first compartment being detachably connected to the third compartment wall of the second compartment; the fourth compartment wall of the first compartment being detachably connected to the fourth compartment wall of the second compartment; the first compartment including a first compartment ceiling; the first compartment ceiling being connected to the first compartment wall of the first compartment by a second hinge mechanism; the first compartment ceiling including a transparent window; the second compartment wall of the first compartment including an audio window; the first compartment floor including an automated external defibrillator securing mechanism for securing an automated external defibrillator to the first compartment floor.

The second compartment wall of the first compartment may be detachably connected to the second compartment wall of the second compartment by a zipper mechanism; the third compartment wall of the first compartment may be detachably connected to the third compartment wall of the second compartment by the zipper mechanism; and the fourth compartment wall of the first compartment may be detachably connected to the fourth compartment wall of the second compartment by the zipper mechanism.

The first compartment ceiling may be detachably connected to the second compartment wall of the first compartment by a zipper mechanism; the first compartment ceiling may be detachably connected to the third compartment wall of the first compartment by the zipper mechanism; and the first compartment ceiling may be detachably connected to the fourth compartment wall of the first compartment by the zipper mechanism.

The first compartment ceiling may be detachably connected to the second compartment wall of the first compartment by a second zipper mechanism; the first compartment ceiling may be detachably connected to the third compartment wall of the first compartment by the second zipper mechanism; and the first compartment ceiling may be detachably connected to the fourth compartment wall of the first compartment by the second zipper mechanism.

The first compartment may include a handle located on an outer surface of the first compartment wall of the first compartment. The first compartment ceiling may include a secured pocket. The first compartment floor may include a secured pocket; the secured pocket is located on a surface of the first compartment floor which surface of the first compartment floor forms a ceiling of the second compartment. The second compartment may include a removable panel having secured pockets; the removable panel of the second compartment being attached to the first compartment wall of the second compartment. The removable panel of the second compartment may be detachably attached to the first compartment wall of the second compartment.

The second compartment may include a removable panel having secured pockets; the removable panel of the second compartment being attached to the first compartment wall of the second compartment. The removable panel of the second compartment may be detachably attached to the first compartment wall of the second compartment. The removable panel of the second compartment may be removable from the second compartment when the third compartment wall of the first compartment is detached from the third compartment wall of the second compartment.

The second compartment floor may include a secured pocket. The first compartment may include a power receptacle to provide electrical power to an electrical device within the automated external defibrillator soft carrying case. The first compartment wall, the second compartment wall, the third compartment wall, and the fourth compartment wall of the first compartment may include an outer shell, an inner shell, and padding material located between the outer shell and the inner shell; and the first compartment wall, the second compartment wall, the third compartment wall, and the fourth compartment wall of the second compartment may include an outer shell, an inner shell, and padding material located between the outer shell and the inner shell. The first compartment ceiling may include an outer shell, an inner shell, and padding material located between the outer shell and the inner shell.

An automated external defibrillator carrying case, comprising a first compartment having first, second, third, and fourth compartment walls and a first compartment floor; and a second compartment having first, second, third, and fourth second compartment walls and a first compartment floor; the first compartment wall of the first compartment being connected to the first compartment wall of the second compartment by a first hinge mechanism; the second compartment wall of the first compartment being connected to the second compartment wall of the second compartment; the third compartment wall of the first compartment being detachably connected to the third compartment wall of the second compartment; the fourth compartment wall of the first compartment being connected to the fourth compartment wall of the second compartment; the second compartment wall of the second compartment being detachably connected to the third compartment wall of the second compartment; the fourth compartment wall of the second compartment being detachably connected to the third compartment wall of the second compartment; the first compartment including a first compartment ceiling; the first compartment ceiling being connected to the first compartment wall of the first compartment by a second hinge mechanism; the first compartment ceiling including a transparent window; the second compartment wall of the first compartment including an audio window; the first compartment floor including an automated external defibrillator securing mechanism for securing an automated external defibrillator to the first compartment floor.

The third compartment wall of the first compartment may be detachably connected to the third compartment wall of the second compartment by a zipper mechanism. The third compartment wall of the second compartment may be detachably connected to the second compartment wall of the second compartment by the zipper mechanism. The fourth compartment wall of the second compartment may be detachably connected to the third compartment wall of the second compartment by the zipper mechanism.

It will be appreciated that several of the above-disclosed embodiments and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the description above and the following claims.

What is claimed is:

1. An automated external defibrillator soft carrying case for preventing the automated external defibrillator soft carrying case from lifting off a surface when operating an automated external defibrillator while the automated external defibrillator is securely located in the automated external defibrillator soft carrying case, comprising:

a first compartment having first, second, third, and fourth compartment walls and a first compartment floor; and a second compartment having first, second, third, and fourth compartment walls and a second compartment floor;

said first compartment wall of said first compartment being connected to said first compartment wall of said second compartment by a first hinge mechanism;

said second compartment wall of said first compartment being detachably connected to said second compartment wall of said second compartment;

said third compartment wall of said first compartment being detachably connected to said third compartment wall of said second compartment;

said fourth compartment wall of said first compartment being detachably connected to said fourth compartment wall of said second compartment;

said first compartment including a first compartment ceiling;

said first compartment ceiling being connected to said first compartment wall of said first compartment by a second hinge mechanism;

said first compartment ceiling including a transparent window;

said second compartment wall of said first compartment including an audio window;

said first compartment floor including an automated external defibrillator securing mechanism for securing an automated external defibrillator to said first compartment floor and for preventing, when said second compartment floor is on a surface, said second compartment floor from lifting off the surface, when operating an automated external defibrillator, when said automated external defibrillator securing mechanism secures the automated external defibrillator to said first compartment floor.

2. The automated external defibrillator soft carrying case, as claimed in claim 1, wherein said second compartment wall of said first compartment is detachably connected to said second compartment wall of said second compartment by a zipper mechanism;

said third compartment wall of said first compartment is detachably connected to said third compartment wall of said second compartment by said zipper mechanism; and said fourth compartment wall of said first compartment is detachably connected to said fourth compartment wall of said second compartment by said zipper mechanism.

3. The automated external defibrillator soft carrying case, as claimed in claim 1, wherein said first compartment ceiling is detachably connected to said second compartment wall of said first compartment by a zipper mechanism;

said first compartment ceiling is detachably connected to said third compartment wall of said first compartment by said zipper mechanism; and said first compartment ceiling is detachably connected to said fourth compartment wall of said first compartment by said zipper mechanism.

4. The automated external defibrillator soft carrying case, as claimed in claim 2, wherein said first compartment ceiling is detachably connected to said second compartment wall of said first compartment by a second zipper mechanism;

said first compartment ceiling is detachably connected to said third compartment wall of said first compartment by said second zipper mechanism; and said first compartment ceiling is detachably connected to said fourth compartment wall of said first compartment by said second zipper mechanism.

5. The automated external defibrillator soft carrying case, as claimed in claim 1, wherein said first compartment includes a handle located on an outer surface of said first compartment wall of said first compartment.

6. The automated external defibrillator soft carrying case, as claimed in claim 1, wherein said first compartment ceiling includes a secured pocket.

7. The automated external defibrillator soft carrying case, as claimed in claim 1, wherein said first compartment floor includes a secured pocket, said secured pocket is located on a surface of said first compartment floor which surface of said first compartment floor forms a ceiling of said second compartment.

8. The automated external defibrillator soft carrying case, as claimed in claim 1, wherein said second compartment includes a removable panel having secured pockets;
said removable panel of said second compartment being attached to said first compartment wall of said second compartment.

9. The automated external defibrillator soft carrying case, as claimed in claim 8, wherein said removable panel of said second compartment is detachably attached to said first compartment wall of said second compartment.

10. The automated external defibrillator soft carrying case, as claimed in claim 2, wherein said second compartment includes a removable panel having secured pockets;
said removable panel of said second compartment being attached to said first compartment wall of said second compartment.

11. The automated external defibrillator soft carrying case, as claimed in claim 10, wherein said removable panel of said second compartment is detachably attached to said first compartment wall of said second compartment.

12. The automated external defibrillator soft carrying case, as claimed in claim 11, wherein said removable panel of said second compartment is removable from said second compartment when said third compartment wall of said first compartment is detached from said third compartment wall of said second compartment.

13. The automated external defibrillator soft carrying case, as claimed in claim 1, wherein said second compartment floor includes a secured pocket.

14. The automated external defibrillator soft carrying case, as claimed in claim 1, wherein said first compartment includes a power interface to provide electrical power to an electrical device within the automated external defibrillator soft carrying case.

15. The automated external defibrillator soft carrying case, as claimed in claim 1, wherein said first compartment includes a power interface to provide electrical power to an automated external defibrillator within the automated external defibrillator soft carrying case.

16. The automated external defibrillator soft carrying case, as claimed in claim 1, wherein said first compartment includes a power interface to provide electrical power to heating element within the automated external defibrillator soft carrying case.

17. The automated external defibrillator soft carrying case, as claimed in claim 1, wherein said first compartment wall, said second compartment wall, said third compartment wall, and said fourth compartment wall of said first compartment include an outer shell, an inner shell, and padding material located between said outer shell and said inner shell; and said first compartment wall, said second compartment wall, said third compartment wall, and said fourth compartment wall of said second compartment include an outer shell, an inner shell, and padding material located between said outer shell and said inner shell.

18. The automated external defibrillator soft carrying case, as claimed in claim 1, wherein said first compartment ceiling includes an outer shell, an inner shell, and padding material located between said outer shell and said inner shell.

19. An automated external defibrillator carrying case for preventing the automated external defibrillator soft carrying case from lifting off a surface when operating an automated external defibrillator while the automated external defibrillator is securely located in the automated external defibrillator soft carrying case, comprising:
a first compartment having first, second, third, and fourth compartment walls and a first compartment floor; and
a second compartment having first, second, third, and fourth compartment walls and a second compartment floor;
said first compartment wall of said first compartment being connected to said first compartment wall of said second compartment by a first hinge mechanism;
said second compartment wall of said first compartment being connected to said second compartment wall of said second compartment;
said third compartment wall of said first compartment being detachably connected to said third compartment wall of said second compartment;
said fourth compartment wall of said first compartment being connected to said fourth compartment wall of said second compartment;
said second compartment wall of said second compartment being detachably connected to said third compartment wall of said second compartment;
said fourth compartment wall of said second compartment being detachably connected to said third compartment wall of said second compartment;
said first compartment including a first compartment ceiling;
said first compartment ceiling being connected to said first compartment wall of said first compartment by a second hinge mechanism;
said first compartment ceiling including a transparent window;
said second compartment wall of said first compartment including an audio window;
said first compartment floor including an automated external defibrillator securing mechanism for securing an automated external defibrillator to said first compartment floor and for preventing, when said second compartment floor is on a surface, said second compartment floor from lifting off the surface, when operating an automated external defibrillator, when said automated external defibrillator securing mechanism secures the automated external defibrillator to said first compartment floor.

20. The automated external defibrillator carrying case, as claimed in claim 19, wherein said third compartment wall of said first compartment is detachably connected to said third compartment wall of said second compartment by a zipper mechanism;
said third compartment wall of said second compartment is detachably connected to said second compartment wall of said second compartment by said zipper mechanism; and said fourth compartment wall of said second compartment is detachably connected to said third compartment wall of said second compartment by said zipper mechanism.

* * * * *